(12) United States Patent
Sloan et al.

(10) Patent No.: US 12,397,111 B2
(45) Date of Patent: *Aug. 26, 2025

(54) CONTINUOUS GLUCOSE MONITORING SYSTEM

(71) Applicant: ABBOTT DIABETES CARE INC., Alameda, CA (US)

(72) Inventors: Mark Sloan, Redwood City, CA (US); Marc B. Taub, Mountain View, CA (US); Gary A. Hayter, Oakland, CA (US); Wesley Scott Harper, Alameda, CA (US); Erwin S. Budiman, Fremont, CA (US); Charles Wei, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/941,586

(22) Filed: Sep. 9, 2022

(65) Prior Publication Data

US 2023/0001090 A1 Jan. 5, 2023

Related U.S. Application Data

(60) Continuation of application No. 17/567,684, filed on Jan. 3, 2022, which is a continuation of application
(Continued)

(51) Int. Cl.
*G08B 21/02* (2006.01)
*A61B 5/00* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
USPC .............. 340/573.1, 538.13, 539.12, 539.11, 340/539.22, 545.3, 555, 588, 691.6, 691.3
See application file for complete search history.

(56) References Cited

U.S. PATENT DOCUMENTS 3,581,062 A 5/1971 Aston
3,926,760 A 12/1975 Allen et al.
(Continued)

FOREIGN PATENT DOCUMENTS

CA 2468577 6/2003
CA 2678336 5/2008
(Continued)

OTHER PUBLICATIONS

U.S. Appl. No. 61/246,630, filed Sep. 29, 2009, Shadforth, et al.
(Continued)

*Primary Examiner* — Daniel Previl
(74) *Attorney, Agent, or Firm* — ONE LLP

(57) ABSTRACT

Methods and systems for delaying alarms that include detecting an analyte level using an analyte sensor; and delaying the annunciation of an analyte alarm after the analyte level crosses an analyte threshold, wherein the delay is based on one or both of (1) a magnitude of difference between the analyte level and the analyte threshold and (2) a duration of time in which the analyte level has crossed the analyte threshold.

30 Claims, 3 Drawing Sheets

Related U.S. Application Data

No. 16/560,497, filed on Sep. 4, 2019, now Pat. No. 11,213,622, which is a continuation of application No. 15/282,688, filed on Sep. 30, 2016, now abandoned, which is a division of application No. 14/076,109, filed on Nov. 8, 2013, now abandoned, which is a continuation of application No. 12/785,144, filed on May 21, 2010, now Pat. No. 8,597,274.

(60) Provisional application No. 61/180,649, filed on May 22, 2009.

(51) Int. Cl.
    *A61B 5/145*     (2006.01)
    *A61M 5/142*     (2006.01)
    *A61M 5/172*     (2006.01)
    *G08B 21/04*     (2006.01)
    *G08B 21/18*     (2006.01)
    *G16H 20/17*     (2018.01)
    *G16H 50/50*     (2018.01)
    *G16H 40/67*     (2018.01)

(52) U.S. Cl.
    CPC ............. *A61B 5/746* (2013.01); *A61M 5/142* (2013.01); *G08B 21/0453* (2013.01); *G08B 21/182* (2013.01); *G16H 20/17* (2018.01); *G16H 50/50* (2018.01); *A61M 2005/14296* (2013.01); *A61M 2205/18* (2013.01); *A61M 2205/3569* (2013.01); *A61M 2205/52* (2013.01); *A61M 2230/201* (2013.01); *G16H 40/67* (2018.01)

(56) References Cited

U.S. PATENT DOCUMENTS

| | | |
|---|---|---|
| 3,949,388 A | 4/1976 | Fuller |
| 3,960,497 A | 6/1976 | Acord et al. |
| 4,033,330 A | 7/1977 | Willis et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,462,048 A | 7/1984 | Ross |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,942,877 A | 7/1990 | Sakai et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,328,460 A | 7/1994 | Lord et al. |
| 5,340,722 A | 8/1994 | Wolfbeis et al. |
| 5,342,789 A | 8/1994 | Chick et al. |
| 5,354,449 A | 10/1994 | Band |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,555,190 A | 9/1996 | Derby et al. |
| 5,564,434 A | 10/1996 | Halperin et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,653,239 A | 8/1997 | Pompei et al. |
| 5,660,163 A | 8/1997 | Schulman et al. |
| 5,665,065 A | 9/1997 | Colman et al. |
| 5,665,222 A | 9/1997 | Heller et al. |
| 5,711,001 A | 1/1998 | Bussan et al. |
| 5,711,861 A | 1/1998 | Ward et al. |
| 5,720,293 A | 2/1998 | Quinn et al. |
| 5,726,646 A | 3/1998 | Bane et al. |

(56) References Cited

U.S. PATENT DOCUMENTS

| | | |
|---|---|---|
| 5,733,259 A | 3/1998 | Valcke et al. |
| 5,735,285 A | 4/1998 | Albert et al. |
| 5,748,103 A | 5/1998 | Flach et al. |
| 5,772,586 A | 6/1998 | Heinonen et al. |
| 5,791,344 A | 8/1998 | Schulman et al. |
| 5,822,715 A | 10/1998 | Worthington et al. |
| 5,899,855 A | 5/1999 | Brown |
| 5,914,026 A | 6/1999 | Blubaugh, Jr. et al. |
| 5,919,141 A | 7/1999 | Money et al. |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,973,613 A | 10/1999 | Reis et al. |
| 5,987,343 A | 11/1999 | Kinast |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,032,119 A | 2/2000 | Brown et al. |
| 6,049,727 A | 4/2000 | Crothall |
| 6,052,565 A | 4/2000 | Ishikura et al. |
| 6,066,243 A | 5/2000 | Anderson et al. |
| 6,066,847 A | 5/2000 | Rosenthal |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,308,089 B1 | 10/2001 | von der Ruhr et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,510,344 B1 | 1/2003 | Halpern |
| 6,514,718 B2 | 2/2003 | Heller et al. |
| 6,515,273 B2 | 2/2003 | Al-Ali |
| 6,544,212 B2 | 4/2003 | Galley et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,631,281 B1 | 10/2003 | Kastle |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,650,471 B2 | 11/2003 | Doi |
| 6,654,625 B1 | 11/2003 | Say et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,025 B1 | 5/2004 | Platt |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |

(56) References Cited

U.S. PATENT DOCUMENTS

| | | |
|---|---|---|
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,046,153 B2 | 5/2006 | Oja et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Xu et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,155,729 B1 | 12/2006 | Andrew et al. |
| 7,167,818 B2 | 1/2007 | Brown |
| 7,171,274 B2 | 1/2007 | Starkweather et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,241,266 B2 | 7/2007 | Zhou et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,301,463 B1 | 11/2007 | Paterno |
| 7,310,544 B2 | 12/2007 | Brister et al. |
| 7,317,938 B2 | 1/2008 | Lorenz et al. |
| 7,335,294 B2 | 2/2008 | Heller et al. |
| 7,344,500 B2 | 3/2008 | Talbot et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,399,277 B2 | 7/2008 | Saidara et al. |
| 7,401,111 B1 | 7/2008 | Batman et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,547,281 B2 | 6/2009 | Hayes et al. |
| 7,569,030 B2 | 8/2009 | Lebel et al. |
| 7,577,469 B1 | 8/2009 | Aronowitz et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,670,263 B2 | 3/2010 | Ellis et al. |
| 7,684,872 B2 | 3/2010 | Carney et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,711,493 B2 | 5/2010 | Bartkowiak et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,751,864 B2 | 7/2010 | Buck, Jr. |
| 7,766,829 B2 | 8/2010 | Sloan et al. |
| 7,768,387 B2 | 8/2010 | Fennell et al. |
| 7,774,145 B2 | 8/2010 | Bruaker et al. |
| 7,778,680 B2 | 8/2010 | Goode, Jr. et al. |
| 7,785,256 B1 | 8/2010 | Koh |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode et al. |
| 7,842,174 B2 | 11/2010 | Zhou et al. |
| 7,857,760 B2 | 12/2010 | Brister et al. |
| 7,885,697 B2 | 2/2011 | Brister et al. |
| 7,885,698 B2 | 2/2011 | Feldman et al. |
| 7,889,069 B2 | 2/2011 | Fifolt et al. |
| 7,894,869 B2 | 2/2011 | Hoarau |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,920,907 B2 | 4/2011 | McGarraugh et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,984 B2 | 5/2011 | Brister et al. |
| 7,946,985 B2 | 5/2011 | Mastrototaro et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,976,467 B2 | 7/2011 | Young et al. |
| 7,978,063 B2 | 7/2011 | Baldus et al. |
| 7,996,158 B2 | 8/2011 | Hayter et al. |
| 8,005,524 B2 | 8/2011 | Brauker et al. |
| 8,010,174 B2 | 8/2011 | Goode et al. |
| 8,010,256 B2 | 8/2011 | Oowada |
| 8,060,173 B2 | 11/2011 | Goode, Jr. et al. |

(56) References Cited

U.S. PATENT DOCUMENTS

| | | |
|---|---|---|
| 8,066,639 B2 | 11/2011 | Nelson et al. |
| 8,073,008 B2 * | 12/2011 | Mehta .................. A61M 5/142 |
| | | 370/468 |
| 8,103,471 B2 | 1/2012 | Hayter |
| 8,140,312 B2 | 3/2012 | Hayter et al. |
| 8,160,669 B2 | 4/2012 | Brauker et al. |
| 8,160,900 B2 | 4/2012 | Taub et al. |
| 8,170,803 B2 | 5/2012 | Kamath et al. |
| 8,190,223 B2 | 5/2012 | Al-Ali et al. |
| 8,192,394 B2 | 6/2012 | Estes et al. |
| 8,207,859 B2 | 6/2012 | Enegren et al. |
| 8,216,138 B1 | 7/2012 | McGarraugh et al. |
| 8,216,139 B2 | 7/2012 | Brauker et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,374,667 B2 | 2/2013 | Brauker et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,409,093 B2 | 4/2013 | Bugler |
| 8,444,560 B2 | 5/2013 | Hayter et al. |
| 8,461,985 B2 | 6/2013 | Fennell et al. |
| 8,478,406 B2 | 7/2013 | Burnes et al. |
| 8,478,557 B2 | 7/2013 | Hayter et al. |
| 8,484,005 B2 | 7/2013 | Hayter et al. |
| 8,497,777 B2 | 7/2013 | Harper |
| 8,514,086 B2 | 8/2013 | Harper et al. |
| 8,543,354 B2 | 9/2013 | Luo et al. |
| 8,560,038 B2 | 10/2013 | Hayter et al. |
| 8,567,393 B2 | 10/2013 | Hickle et al. |
| 8,571,808 B2 | 10/2013 | Hayter |
| 8,583,205 B2 | 11/2013 | Budiman et al. |
| 8,597,274 B2 | 12/2013 | Sloan et al. |
| 8,597,570 B2 | 12/2013 | Terashima et al. |
| 8,600,681 B2 | 12/2013 | Hayter et al. |
| 8,608,923 B2 | 12/2013 | Zhou et al. |
| 8,612,163 B2 | 12/2013 | Hayter et al. |
| 8,657,746 B2 | 2/2014 | Roy |
| 8,710,993 B2 | 4/2014 | Hayter et al. |
| 8,730,058 B2 | 5/2014 | Harper |
| 8,734,422 B2 | 5/2014 | Hayter |
| 8,816,862 B2 | 8/2014 | Harper et al. |
| 8,821,792 B2 | 9/2014 | Drucker et al. |
| 8,834,366 B2 | 9/2014 | Hayter et al. |
| 8,845,536 B2 | 9/2014 | Brauker et al. |
| 9,000,914 B2 | 4/2015 | Baker et al. |
| 9,060,719 B2 | 6/2015 | Hayter et al. |
| 9,119,528 B2 | 9/2015 | Cobelli |
| 9,143,569 B2 | 9/2015 | Mensinger et al. |
| 9,178,752 B2 | 11/2015 | Harper |
| 9,186,113 B2 | 11/2015 | Harper et al. |
| 9,215,980 B2 | 12/2015 | Tran et al. |
| 9,226,714 B2 | 1/2016 | Harper et al. |
| 9,289,179 B2 | 3/2016 | Hayter et al. |
| 9,339,197 B2 | 5/2016 | Griswold et al. |
| 9,398,872 B2 | 7/2016 | Hayter et al. |
| 9,408,566 B2 | 8/2016 | Hayter et al. |
| 9,414,775 B2 | 8/2016 | Colvin, Jr. et al. |
| 9,439,586 B2 | 9/2016 | Bugler |
| 9,446,194 B2 | 9/2016 | Kamath et al. |
| 9,452,258 B2 | 9/2016 | Dobbles et al. |
| 9,483,608 B2 | 11/2016 | Hayter et al. |
| 9,549,694 B2 | 1/2017 | Harper et al. |
| 9,558,325 B2 | 1/2017 | Hayter et al. |
| 9,717,421 B2 | 8/2017 | Griswold et al. |
| 9,743,872 B2 | 8/2017 | Hayter et al. |
| 9,801,541 B2 | 10/2017 | Mensinger et al. |
| 9,804,148 B2 | 10/2017 | Hayter et al. |
| 9,814,400 B1 | 11/2017 | Cendrillon et al. |
| 9,814,416 B2 | 11/2017 | Harper et al. |
| 9,833,181 B2 | 12/2017 | Hayter et al. |
| 9,980,140 B1 | 5/2018 | Spencer et al. |
| 10,009,244 B2 | 6/2018 | Harper et al. |
| 10,123,752 B2 | 11/2018 | Harper et al. |
| 10,159,432 B1 | 12/2018 | Pathak et al. |
| 10,209,817 B1 | 2/2019 | Cazzoli et al. |
| 10,264,971 B1 | 4/2019 | Kennedy et al. |
| 10,375,222 B2 | 8/2019 | Mandapaka et al. |
| 10,456,091 B2 | 10/2019 | Harper et al. |
| 10,702,215 B2 | 7/2020 | Hampapuram et al. |
| 10,772,572 B2 | 9/2020 | Harper et al. |
| 10,855,788 B2 | 12/2020 | Arabo et al. |
| 11,213,204 B2 | 1/2022 | Mensinger et al. |
| 11,241,175 B2 | 2/2022 | Sloan et al. |
| 11,991,175 B2 | 5/2024 | Rolfe et al. |
| 2001/0037366 A1 | 11/2001 | Webb et al. |
| 2002/0016534 A1 | 2/2002 | Trepagnier et al. |
| 2002/0016568 A1 * | 2/2002 | Lebel ................ A61M 5/14244 |
| | | 128/904 |
| 2002/0019022 A1 | 2/2002 | Dunn et al. |
| 2002/0032531 A1 | 3/2002 | Mansky et al. |
| 2002/0042090 A1 | 4/2002 | Heller et al. |
| 2002/0045808 A1 | 4/2002 | Ford et al. |
| 2002/0054320 A1 | 5/2002 | Ogino |
| 2002/0057993 A1 | 5/2002 | Maisey et al. |
| 2002/0065454 A1 | 5/2002 | Lebel et al. |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0150959 A1 | 10/2002 | Lejeunne et al. |
| 2002/0156355 A1 | 10/2002 | Gough |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114836 A1 | 6/2003 | Estes et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0163789 A1 | 8/2003 | Blomquist |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0211617 A1 | 11/2003 | Jones |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |

(56) References Cited

U.S. PATENT DOCUMENTS

| | | |
|---|---|---|
| 2004/0063435 A1 | 4/2004 | Sakamoto et al. |
| 2004/0064068 A1 | 4/2004 | DeNuzzio et al. |
| 2004/0078219 A1 | 4/2004 | Kaylor et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0158294 A1 | 8/2004 | Thompson |
| 2004/0162477 A1 | 8/2004 | Okamura et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0038674 A1 | 2/2005 | Braig et al. |
| 2005/0038680 A1 | 2/2005 | McMahon et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0075675 A1 | 4/2005 | Mulligan et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soy et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0148890 A1 | 7/2005 | Hastings |
| 2005/0154271 A1 | 7/2005 | Rasdal et al. |
| 2005/0171513 A1 | 8/2005 | Mann et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1* | 9/2005 | Spital ............ G06F 8/60 375/368 |
| 2005/0196821 A1 | 9/2005 | Monfre et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0209515 A1 | 9/2005 | Hockersmith et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0277164 A1 | 12/2005 | Drucker et al. |
| 2005/0277912 A1 | 12/2005 | John |
| 2005/0280521 A1 | 12/2005 | Mizumaki |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0011474 A1 | 1/2006 | Schulein et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0019397 A1 | 1/2006 | Soykan |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0087655 A1 | 4/2006 | Augustine et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0222566 A1 | 10/2006 | Brauker et al. |
| 2006/0224109 A1 | 10/2006 | Steil et al. |

(56) References Cited

U.S. PATENT DOCUMENTS

| | | |
|---|---|---|
| 2006/0224141 A1 | 10/2006 | Rush et al. |
| 2006/0229511 A1 | 10/2006 | Fein et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0264785 A1 | 11/2006 | Dring et al. |
| 2006/0270421 A1 | 11/2006 | Phillips et al. |
| 2006/0272652 A1 | 12/2006 | Stocker et al. |
| 2006/0276771 A1 | 12/2006 | Galley et al. |
| 2006/0290496 A1 | 12/2006 | Peeters et al. |
| 2006/0293607 A1 | 12/2006 | Alt et al. |
| 2007/0015976 A1 | 1/2007 | Miesel et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0038053 A1 | 2/2007 | Berner et al. |
| 2007/0052965 A1 | 3/2007 | Pesach et al. |
| 2007/0060796 A1 | 3/2007 | Kim |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0107973 A1 | 5/2007 | Jiang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149874 A1 | 6/2007 | Say et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0170054 A2 | 7/2007 | Wilsey |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179370 A1 | 8/2007 | Say et al. |
| 2007/0191701 A1 | 8/2007 | Feldman et al. |
| 2007/0191702 A1 | 8/2007 | Yodfat et al. |
| 2007/0197889 A1 | 8/2007 | Brauker et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0249922 A1 | 10/2007 | Peyser et al. |
| 2007/0255116 A1 | 11/2007 | Mehta et al. |
| 2007/0255166 A1 | 11/2007 | Carney et al. |
| 2007/0255321 A1 | 11/2007 | Gerber et al. |
| 2007/0255348 A1 | 11/2007 | Holtzclaw |
| 2007/0255352 A1 | 11/2007 | Roline et al. |
| 2007/0255353 A1 | 11/2007 | Reinke et al. |
| 2007/0265666 A1 | 11/2007 | Roberts et al. |
| 2007/0265668 A1 | 11/2007 | Reinke et al. |
| 2007/0265671 A1 | 11/2007 | Roberts et al. |
| 2007/0265674 A1 | 11/2007 | Olson et al. |
| 2007/0270672 A1 | 11/2007 | Hayter et al. |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0087544 A1 | 4/2008 | Zhou et al. |
| 2008/0092638 A1 | 4/2008 | Brenneman et al. |
| 2008/0097246 A1 | 4/2008 | Stafford |
| 2008/0097289 A1 | 4/2008 | Steil et al. |
| 2008/0103447 A1 | 5/2008 | Reggiardo et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119708 A1 | 5/2008 | Budiman |
| 2008/0119710 A1 | 5/2008 | Reggiardo et al. |
| 2008/0125701 A1 | 5/2008 | Moberg et al. |
| 2008/0139910 A1 | 6/2008 | Mastrototaro et al. |
| 2008/0149821 A1 | 6/2008 | Senko |
| 2008/0154099 A1 | 6/2008 | Aspel et al. |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0172026 A1 | 7/2008 | Blomquist |
| 2008/0172030 A1 | 7/2008 | Blomquist |
| 2008/0172031 A1 | 7/2008 | Blomquist |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201169 A1 | 8/2008 | Galasso et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |

(56) References Cited

U.S. PATENT DOCUMENTS

| | | |
|---|---|---|
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0221930 A1 | 9/2008 | Wekell et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234562 A1 | 9/2008 | Jina |
| 2008/0234943 A1 | 9/2008 | Ray et al. |
| 2008/0234992 A1 | 9/2008 | Ray et al. |
| 2008/0235053 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saudara et al. |
| 2008/0255635 A1 | 10/2008 | Bettesh et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0278331 A1 | 11/2008 | Hayter et al. |
| 2008/0278332 A1 | 11/2008 | Fennel et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006129 A1 | 1/2009 | Thukral et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0030641 A1 | 1/2009 | Fjield et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054749 A1 | 2/2009 | He |
| 2009/0054750 A1 | 2/2009 | Jennewine |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0069642 A1 | 3/2009 | Gao et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0093687 A1 | 4/2009 | Telfort et al. |
| 2009/0099436 A1 | 4/2009 | Brister et al. |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112154 A1 | 4/2009 | Montgomery et al. |
| 2009/0112478 A1 | 4/2009 | Mueller, Jr. et al. |
| 2009/0112626 A1 | 4/2009 | Talbot et al. |
| 2009/0114811 A1 | 5/2009 | Landgraf |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149717 A1 | 6/2009 | Brauer et al. |
| 2009/0149728 A1 | 6/2009 | Van Antwerp et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0210249 A1 | 8/2009 | Rasch-Menges et al. |
| 2009/0216100 A1 | 8/2009 | Ebner et al. |
| 2009/0216102 A1 | 8/2009 | Say et al. |
| 2009/0216103 A1 | 8/2009 | Brister et al. |
| 2009/0221890 A1 | 9/2009 | Saffer et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247849 A1 | 10/2009 | McCutcheon et al. |
| 2009/0247855 A1 | 10/2009 | Boock et al. |
| 2009/0247856 A1 | 10/2009 | Boock et al. |

(56) References Cited

U.S. PATENT DOCUMENTS

| | | |
|---|---|---|
| 2009/0247857 A1 | 10/2009 | Harper et al. |
| 2009/0254037 A1 | 10/2009 | Bryant et al. |
| 2009/0257911 A1 | 10/2009 | Thomas et al. |
| 2009/0275815 A1 | 11/2009 | Bickoff et al. |
| 2009/0275887 A1 | 11/2009 | Estes |
| 2009/0287073 A1 | 11/2009 | Boock et al. |
| 2009/0287074 A1 | 11/2009 | Shults et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0312615 A1 | 12/2009 | Caduff et al. |
| 2009/0312622 A1 | 12/2009 | Regittnig |
| 2009/0318792 A1 | 12/2009 | Fennell et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0017141 A1 | 1/2010 | Campbell et al. |
| 2010/0022855 A1 | 1/2010 | Brauker et al. |
| 2010/0022988 A1 | 1/2010 | Wochner et al. |
| 2010/0023081 A1 | 1/2010 | Audet et al. |
| 2010/0023291 A1 | 1/2010 | Hayter et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0033303 A1 | 2/2010 | Dugan et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045425 A1 | 2/2010 | Chivallier |
| 2010/0045465 A1 | 2/2010 | Brauker et al. |
| 2010/0049024 A1 | 2/2010 | Saint et al. |
| 2010/0049164 A1 | 2/2010 | Estes |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0064764 A1 | 3/2010 | Hayter et al. |
| 2010/0075353 A1 | 3/2010 | Heaton |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0093786 A1 | 4/2010 | Watanabe et al. |
| 2010/0094111 A1 | 4/2010 | Heller et al. |
| 2010/0094251 A1 | 4/2010 | Estes et al. |
| 2010/0095229 A1 | 4/2010 | Dixon et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0152548 A1 | 6/2010 | Koski |
| 2010/0152554 A1 | 6/2010 | Steine et al. |
| 2010/0152561 A1 | 6/2010 | Goodnow et al. |
| 2010/0160757 A1 | 6/2010 | Weinert et al. |
| 2010/0160759 A1 | 6/2010 | Celentano et al. |
| 2010/0161236 A1 | 6/2010 | Cohen et al. |
| 2010/0168538 A1 | 7/2010 | Keenan et al. |
| 2010/0168546 A1 | 7/2010 | Kamath et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0174266 A1 | 7/2010 | Estes |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0185175 A1 | 7/2010 | Kamen et al. |
| 2010/0191082 A1 | 7/2010 | Brister et al. |
| 2010/0191085 A1 | 7/2010 | Budiman |
| 2010/0191087 A1 | 7/2010 | Talbot et al. |
| 2010/0191472 A1 | 7/2010 | Doniger |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0240976 A1 | 9/2010 | Goode et al. |
| 2010/0249530 A1 | 9/2010 | Rankers et al. |
| 2010/0259543 A1 | 10/2010 | Tarassenko et al. |
| 2010/0261987 A1 | 10/2010 | Kamath et al. |
| 2010/0265073 A1 | 10/2010 | Harper et al. |
| 2010/0268157 A1 | 10/2010 | Wehba et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0277342 A1 | 11/2010 | Sicurello et al. |
| 2010/0280341 A1 | 11/2010 | Boock et al. |
| 2010/0280441 A1 | 11/2010 | Wlinska et al. |
| 2010/0280782 A1 | 11/2010 | Harper et al. |
| 2010/0286496 A1 | 11/2010 | Simpson et al. |
| 2010/0292948 A1 | 11/2010 | Feldman et al. |
| 2010/0298684 A1 | 11/2010 | Leach et al. |
| 2010/0305965 A1 | 12/2010 | Benjamin et al. |
| 2010/0313105 A1 | 12/2010 | Nekoomaram et al. |
| 2010/0324403 A1 | 12/2010 | Brister et al. |
| 2010/0327057 A1 | 12/2010 | Medina et al. |
| 2010/0331644 A1 | 12/2010 | Neale et al. |
| 2010/0331648 A1 | 12/2010 | Kamath et al. |
| 2010/0331651 A1 | 12/2010 | Groll |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009724 A1 | 1/2011 | Hill et al. |
| 2011/0009727 A1 | 1/2011 | Mensinger et al. |
| 2011/0009813 A1 | 1/2011 | Rankers et al. |
| 2011/0010257 A1 | 1/2011 | Hill et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |

(56) References Cited

U.S. PATENT DOCUMENTS

| | | |
|---|---|---|
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029269 A1 | 2/2011 | Hayter et al. |
| 2011/0031986 A1 | 2/2011 | Bhat et al. |
| 2011/0036714 A1 | 2/2011 | Zhou et al. |
| 2011/0040163 A1 | 2/2011 | Telson et al. |
| 2011/0046467 A1 | 2/2011 | Simpson et al. |
| 2011/0053121 A1 | 3/2011 | Heaton |
| 2011/0054282 A1 | 3/2011 | Nekoomaram et al. |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0105873 A1 | 5/2011 | Feldman et al. |
| 2011/0106011 A1 | 5/2011 | Cinar et al. |
| 2011/0112696 A1 | 5/2011 | Yodfat et al. |
| 2011/0118579 A1 | 5/2011 | Goode et al. |
| 2011/0118580 A1 | 5/2011 | Goode et al. |
| 2011/0123971 A1 | 5/2011 | Berkowitz et al. |
| 2011/0124992 A1 | 5/2011 | Brauker et al. |
| 2011/0124996 A1 | 5/2011 | Reinke et al. |
| 2011/0124997 A1 | 5/2011 | Goode et al. |
| 2011/0125410 A1 | 5/2011 | Goode et al. |
| 2011/0126188 A1 | 5/2011 | Bernstein et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0131307 A1 | 6/2011 | El Bazzal et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0163880 A1 | 7/2011 | Halff et al. |
| 2011/0163881 A1 | 7/2011 | Halff et al. |
| 2011/0173308 A1 | 7/2011 | Gutekunst |
| 2011/0178378 A1 | 7/2011 | Brister et al. |
| 2011/0178717 A1 | 7/2011 | Goodnow et al. |
| 2011/0184265 A1 | 7/2011 | Hayter |
| 2011/0184267 A1 | 7/2011 | Duke et al. |
| 2011/0184268 A1 | 7/2011 | Taub |
| 2011/0184752 A1 | 7/2011 | Ray et al. |
| 2011/0190614 A1 | 8/2011 | Brister et al. |
| 2011/0193704 A1 | 8/2011 | Harper et al. |
| 2011/0196217 A1 | 8/2011 | Myoujou et al. |
| 2011/0201910 A1 | 8/2011 | Rasdal et al. |
| 2011/0201911 A1 | 8/2011 | Johnson et al. |
| 2011/0202495 A1 | 8/2011 | Gawlick |
| 2011/0208027 A1 | 8/2011 | Wagner et al. |
| 2011/0218414 A1 | 9/2011 | Kamath et al. |
| 2011/0224523 A1 | 9/2011 | Budiman |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0237960 A1 | 9/2011 | Rantala |
| 2011/0253533 A1 | 10/2011 | Shults et al. |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319739 A1 | 12/2011 | Kamath et al. |
| 2011/0320130 A1 | 12/2011 | Valdes et al. |
| 2011/0320167 A1 | 12/2011 | Budiman |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0108931 A1 | 5/2012 | Taub |
| 2012/0108934 A1 | 5/2012 | Valdes et al. |
| 2012/0157801 A1 | 6/2012 | Hoss et al. |
| 2012/0165626 A1 | 6/2012 | Irina et al. |
| 2012/0165640 A1 | 6/2012 | Galley et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0173200 A1 | 7/2012 | Breton et al. |
| 2012/0185416 A1 | 7/2012 | Baras et al. |
| 2012/0186997 A1 | 7/2012 | Li et al. |
| 2012/0242501 A1 | 9/2012 | Tran et al. |
| 2012/0245447 A1 | 9/2012 | Karan et al. |
| 2012/0262298 A1 | 10/2012 | Bohm et al. |
| 2012/0283542 A1 | 11/2012 | McGarraugh |
| 2012/0313785 A1 | 12/2012 | Hanson et al. |
| 2012/0318670 A1 | 12/2012 | Karinka et al. |
| 2012/0323099 A1 | 12/2012 | Mothilal et al. |
| 2013/0035575 A1 | 2/2013 | Mayou et al. |
| 2013/0043974 A1 | 2/2013 | Hyde et al. |
| 2013/0085358 A1 | 4/2013 | Crouther et al. |
| 2013/0109944 A1 | 5/2013 | Sparacino et al. |
| 2013/0132330 A1 | 5/2013 | Hurwitz et al. |
| 2013/0137953 A1 | 5/2013 | Harper et al. |
| 2013/0198685 A1 | 8/2013 | Bernini et al. |
| 2013/0217979 A1 | 8/2013 | Blackadar et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2013/0245547 A1 | 9/2013 | El-Khatib et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0298063 A1 | 11/2013 | Joy et al. |
| 2013/0324823 A1 | 12/2013 | Koski et al. |
| 2014/0001044 A1 | 1/2014 | Ecoff et al. |
| 2014/0005499 A1 | 1/2014 | Catt et al. |
| 2014/0012511 A1 | 1/2014 | Mensinger et al. |
| 2014/0018644 A1 | 1/2014 | Colvin, Jr. et al. |
| 2014/0039383 A1 | 2/2014 | Dobbles et al. |
| 2014/0046160 A1 | 2/2014 | Terashima et al. |
| 2014/0052091 A1 | 2/2014 | Dobbles et al. |
| 2014/0052092 A1 | 2/2014 | Dobbles et al. |
| 2014/0052722 A1 | 2/2014 | Bertsimas et al. |
| 2014/0058240 A1 | 2/2014 | Mothilal et al. |
| 2014/0088392 A1 | 3/2014 | Bernstein et al. |
| 2014/0088393 A1 | 3/2014 | Bernstein et al. |
| 2014/0266776 A1 | 9/2014 | Miller et al. |
| 2014/0266785 A1 | 9/2014 | Miller et al. |
| 2014/0273858 A1 | 9/2014 | Panther et al. |
| 2014/0275898 A1 | 9/2014 | Taub et al. |
| 2014/0278189 A1 | 9/2014 | Vanslyke et al. |
| 2014/0313052 A1 | 10/2014 | Yarger et al. |
| 2014/0350359 A1 | 11/2014 | Tankiewicz et al. |
| 2014/0350369 A1 | 11/2014 | Budiman et al. |
| 2014/0350371 A1 | 11/2014 | Blomquist et al. |
| 2014/0379273 A1 | 12/2014 | Petisce et al. |
| 2015/0018643 A1 | 1/2015 | Cole et al. |
| 2015/0094914 A1* | 4/2015 | Abreu ............... B60H 1/00742 701/1 |
| 2015/0118658 A1 | 4/2015 | Mayou et al. |
| 2015/0119655 A1 | 4/2015 | Mayou et al. |
| 2015/0120317 A1 | 4/2015 | Mayou et al. |
| 2015/0123810 A1 | 5/2015 | Hernandez-Rosas et al. |
| 2015/0141770 A1 | 5/2015 | Rastogi et al. |
| 2015/0170504 A1 | 6/2015 | Jooste |
| 2015/0205947 A1 | 7/2015 | Berman et al. |
| 2015/0207796 A1 | 7/2015 | Love et al. |
| 2015/0241407 A1 | 8/2015 | Ou et al. |
| 2015/0289821 A1 | 10/2015 | Rack-Gomer et al. |
| 2015/0292856 A1 | 10/2015 | Ganton et al. |
| 2016/0029931 A1 | 2/2016 | Salas-Boni et al. |
| 2016/0100807 A1 | 4/2016 | Johnson et al. |
| 2016/0101232 A1 | 4/2016 | Kamath et al. |

(56) References Cited

U.S. PATENT DOCUMENTS

| | | |
|---|---|---|
| 2016/0103604 A1 | 4/2016 | Johnson et al. |
| 2016/0129182 A1 | 5/2016 | Schuster et al. |
| 2016/0232322 A1 | 8/2016 | Mensinger et al. |
| 2016/0245791 A1 | 8/2016 | Hayter et al. |
| 2016/0262670 A1 | 9/2016 | Wasson et al. |
| 2016/0302701 A1 | 10/2016 | Bhavaraju et al. |
| 2016/0317069 A1 | 11/2016 | Hayter et al. |
| 2016/0321428 A1 | 11/2016 | Rogers |
| 2016/0324463 A1 | 11/2016 | Simpson et al. |
| 2016/0328990 A1 | 11/2016 | Simpson et al. |
| 2016/0331310 A1 | 11/2016 | Kovatchev |
| 2016/0345830 A1 | 12/2016 | Raisoni et al. |
| 2017/0027515 A1 | 2/2017 | Wiser |
| 2017/0053084 A1 | 2/2017 | McMahon et al. |
| 2017/0086756 A1 | 3/2017 | Harper et al. |
| 2017/0109990 A1 | 4/2017 | Xu et al. |
| 2017/0157774 A1 | 6/2017 | Pathak et al. |
| 2017/0169358 A1 | 6/2017 | Choi et al. |
| 2017/0172510 A1 | 6/2017 | Homyk et al. |
| 2017/0185748 A1 | 6/2017 | Budiman et al. |
| 2017/0213145 A1 | 7/2017 | Pathak et al. |
| 2017/0215808 A1 | 8/2017 | Shimol et al. |
| 2017/0249445 A1 | 8/2017 | Devries et al. |
| 2017/0273610 A1 | 9/2017 | Suri et al. |
| 2017/0311903 A1 | 11/2017 | Davis et al. |
| 2018/0039097 A1 | 2/2018 | Gutierrez |
| 2018/0103882 A1 | 4/2018 | Biederman et al. |
| 2018/0109852 A1 | 4/2018 | Mandapaka et al. |
| 2018/0110078 A1 | 4/2018 | Madapaka et al. |
| 2018/0125364 A1 | 5/2018 | DeHennis |
| 2018/0256103 A1 | 9/2018 | Cole et al. |
| 2018/0279928 A1 | 10/2018 | Bohm et al. |
| 2019/0075443 A1 | 3/2019 | Fu et al. |
| 2019/0275234 A1 | 9/2019 | Yang |
| 2019/0295398 A1 | 9/2019 | Khac et al. |
| 2019/0307958 A1 | 10/2019 | Yang |
| 2019/0328340 A1 | 10/2019 | Yang |
| 2020/0275893 A1 | 9/2020 | Burnette et al. |

FOREIGN PATENT DOCUMENTS

| | | |
|---|---|---|
| CA | 2626349 | 9/2008 |
| CA | 2728831 | 7/2011 |
| CA | 2617965 | 10/2011 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 03 903 90 | 10/1990 |
| EP | 0396788 | 11/1990 |
| EP | 0286118 | 1/1995 |
| EP | 1048264 | 11/2000 |
| EP | 1759201 | 3/2007 |
| EP | 2031534 | 3/2009 |
| EP | 1725163 | 12/2010 |
| EP | 2685895 | 9/2012 |
| EP | 3 210 137 B1 | 3/2021 |
| EP | 2914159 B1 | 4/2021 |
| EP | 3 831 282 B1 | 3/2022 |
| EP | 2939158 | 3/2022 |
| EP | 4 070 727 A1 | 10/2022 |
| EP | 4 070 727 B1 | 7/2023 |
| EP | 3988471 B1 | 7/2023 |
| WO | WO1996/025089 | 8/1996 |
| WO | WO1996/035370 | 11/1996 |
| WO | WO1998/035053 | 8/1998 |
| WO | WO1999/027849 | 6/1999 |
| WO | WO1999/028736 | 6/1999 |
| WO | WO1999/056613 | 11/1999 |
| WO | WO2000/049940 | 8/2000 |
| WO | WO2000/059370 | 10/2000 |
| WO | WO 00/78213 A2 | 12/2000 |
| WO | WO2000/074753 | 12/2000 |
| WO | WO2001/05293 5 | 7/2001 |
| WO | WO2001/054753 | 8/2001 |
| WO | WO2002/016905 | 2/2002 |
| WO | WO2003/057027 | 7/2003 |
| WO | WO2003/076893 | 9/2003 |
| WO | WO2003/082091 | 10/2003 |
| WO | WO 2004/006982 A2 | 1/2004 |
| WO | WO2004/009161 | 1/2004 |
| WO | WO2004/060455 | 7/2004 |
| WO | WO2005/057175 | 6/2005 |
| WO | WO2005/065538 | 7/2005 |
| WO | WO2005/065542 | 7/2005 |
| WO | WO2005/121785 | 12/2005 |
| WO | WO2006/020212 | 2/2006 |
| WO | WO2006/024671 | 3/2006 |
| WO | WO2006/072035 | 7/2006 |
| WO | WO2006/079867 | 8/2006 |
| WO | WO2007/019289 | 2/2007 |
| WO | WO2008/030347 | 3/2008 |
| WO | WO2008/048452 | 4/2008 |
| WO | WO2008/052374 | 5/2008 |
| WO | WO2008/062099 | 5/2008 |
| WO | WO2008/086541 | 7/2008 |
| WO | WO2008/130898 | 10/2008 |
| WO | WO2008/144445 | 11/2008 |
| WO | WO 2008/151452 | 12/2008 |
| WO | WO2009/048462 | 4/2009 |
| WO | WO 2009/049252 | 4/2009 |
| WO | WO2009/097594 | 8/2009 |
| WO | WO 2009/136372 | 11/2009 |
| WO | WO2009/146119 | 12/2009 |
| WO | WO2009/146445 | 12/2009 |
| WO | WO2010/062898 | 6/2010 |
| WO | WO2011/000528 | 1/2011 |
| WO | WO2011/026053 | 3/2011 |
| WO | WO2011/041007 | 4/2011 |
| WO | WO2011/060923 | 5/2011 |
| WO | WO2011/104616 | 9/2011 |
| WO | WO 2012/154286 | 11/2012 |
| WO | WO2014/070456 | 5/2014 |
| WO | WO 2014/105631 A2 | 7/2014 |
| WO | WO 2015/069797 | 5/2015 |
| WO | WO2015/153482 | 10/2015 |
| WO | WO 2016/092448 | 6/2016 |
| WO | WO2016/179559 | 11/2016 |
| WO | WO2018/164886 | 9/2018 |

OTHER PUBLICATIONS

U.S. Appl. No. 12/622,520, filed Nov. 20, 2009, Reinke et al.
U.S. Appl. No. 17/567,684 (US 2022-0118180 A1), filed Jan. 3, 2022 (Apr. 21, 2022).
U.S. Appl. No. 16/560,497 (U.S. Pat. No. 11,213,622), filed Sep. 4, 2019 (Jan. 4, 2022).
U.S. Appl. No. 15/282,688 (US 2017-0035969 A1), filed Sep. 30, 2016 (Feb. 9, 2017).
U.S. Appl. No. 14/076,109 (US 2014-0066890 A1), filed Nov. 8, 2013 (Mar. 6, 2014).
U.S. Appl. No. 12/785,144 (U.S. Pat. No. 8,597,274), filed May 21, 2010 (Dec. 3, 2013).
U.S. Appl. No. 16/560,497, Nov. 23, 2021 Issue Fee Payment.
U.S. Appl. No. 16/560,497, Aug. 25, 2021 Notice of Allowance.
U.S. Appl. No. 16/560,497, Aug. 10, 2021 Response to Final Office Action and Request for Continued Examination (RCE).
U.S. Appl. No. 16/560,497, May 10, 2021 Final Office Action.
U.S. Appl. No. 16/560,497, Mar. 17, 2021 Response to Non-Final Office Action.
U.S. Appl. No. 16/560,497, Nov. 23, 2020 Non-Final Office Action.
U.S. Appl. No. 15/282,688, Oct. 10, 2019 Abandonment.
U.S. Appl. No. 15/282,688, Apr. 4, 2019 Non-Final Office Action.
U.S. Appl. No. 14/076,109, Dec. 15, 2016 Abandonment.
U.S. Appl. No. 14/076,109, Jun. 2, 2016 Non-Final Office Action.
U.S. Appl. No. 14/076,109, Apr. 22, 2016 Response to Final Office Action and Request for Continued Examination (RCE).
U.S. Appl. No. 14/076,109, Jan. 22, 2016 Final Office Action.
U.S. Appl. No. 14/076,109, Nov. 9, 2015 Response to Non-Final Office Action.

(56) References Cited

OTHER PUBLICATIONS

U.S. Appl. No. 14/076,109, Jun. 11, 2015 Non-Final Office Action.
U.S. Appl. No. 14/076,109, May 26, 2015 Response to Restriction Requirement.
U.S. Appl. No. 14/076,109, Mar. 24, 2015 Restriction Requirement.
U.S. Appl. No. 12/785,144, Oct. 29, 2013 Issue Fee Payment.
U.S. Appl. No. 12/785,144, Sep. 3, 2013 Notice of Allowance.
U.S. Appl. No. 12/785,144, Jun. 26, 2013 Response to Non-Final Office Action.
U.S. Appl. No. 12/785,144, Mar. 27, 2013 Non-Final Office Action.
U.S. Appl. No. 12/785,144, Mar. 18, 2013 Response to Restriction Requirement.
U.S. Appl. No. 12/785,144, Jan. 18, 2013 Restriction Requirement.
Abbott's Continuous Blood Glucose Monitor Approval Soon, 2006, 3 pages.
About Dexcom—Continuous Glucose Monitoring Company, 2021, 12 pages.
About the Congressional Record, Congress.Gov, Library of Congress, 2022, 3 pages.
Aleppo, G., et al. "REPLACE-BG: A Randomized Trial Comparing Continuous Glucose Monitoring With and Without Routine Blood Glucose Monitoring in Adults With Well-Controlled Type 1 Diabetes" Diabetes Care, 2017, 40:538-545.
Amendment No. 2 to the OUS Commercialization Agreement, 2011, 12 pages.
Amiel, S. A., et al., "Hypoglycaemia in Type 2 diabetes", Diabetic Medicine, 2008, 25:245-254.
Amiel, S. et al., "Training in flexible, intensive insulin management to enable dietary freedom in people with type 1 diabetes: dose adjustment for normal eating (DAFNE) randomized controlled trial" BMJ, 2002, 325; 6 pages.
Animas® Vibe™, the First Integrated Offering from Animas Corporation and Dexcom, Inc, Receives European CE Mark Approval, Products & Operating Company, 2011, 4 pages.
ANZHSN National Horizon Scanning Unit Horizon scanning report, GlucoWatch® G2 Biographer for the non-invasive monitoring of glucose levels, AHTA, 2004, 46 pages.
Armour, J. C., et al., "Application of Chronic Intravascular Blood Glucose Sensor in Dogs", Diabetes, vol. 39, 1990, pp. 1519-1526.
Bailey, T.S. et al., "Reduction in Hemoglobin A1c with Real-Time Continuous Glucose Monitoring: Results from a 12-Week Observational Study" Diabetes Technology & Therapeutics, 2007, 9(3):203-210.
Bennion, N., et al., "Alternate Site Glucose Testing: A Crossover Design", Diabetes Technology & Therapeutics, vol. 4, No. 1, 2002, pp. 25-33.
Bindra, D.S., et al., "Design and in Vitro Studies of a Needle-Type Glucose Sensor for Subcutaneous Monitoring", Analytical Chemistry, vol. 63, No. 17, 1991, pp. 1692-1696.
Blank, T. B., et al., "Clinical Results From a Non-invasive Blood Glucose Monitor", Optical Diagnostics and Sensing of Biological Fluids and Glucose and Cholesterol Monitoring IT, Proceedings of SPIE, vol. 4624, 2002, pp. 1-10.
Bode, B., et al., "Alarms Based on Real-Time Sensor Glucose Values Alert Patients to Hypo- and Hyperglycemia: The Guardian Continuous Monitoring System", Diabetes Technology & Therapeutics, vol. 6, No. 2, 2004, pp. 105-113.
Brooks, S. L., et al., "Development of an On-Line Glucose Sensor for Fermentation Monitoring", Biosensors, vol. 3, 1987/88, pp. 45-56.
Brown, A., et al., "test drive—Dexcom's G4 Platinum CGM", diaTribe Learn, Making Sense of Diabetes, 2012, 4 pages.
Buckingham, B., et al., "Prevention of Nocturnal Hypoglycemia Using Predictive Alarm Algorithms and Insulin Pump Suspension", Diabetes Care, vol. 33, No. 5, 2010, pp. 1013-1017.
Burton, et al., "Urging FDA to act promptly to approve artificial pancreas technologies", Congressional Record, vol. 157, Part 13, 2011, 3 pages.

Cass, A. E., et al., "Ferrocene-Medicated Enzyme Electrode for Amperometric Determination of Glucose", Analytical Chemistry, vol. 56, No. 4, 1984, 667-671.
CGMS® iPro™ Continuous Glucose Recorder, User Guide, Medtronic MiniMed, 2007, 36 pages.
Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.
Children with Diabetes, Report from Diabetes Technology Meeting, 2003, 3 pages.
Choudhary, p et al., "Hypoglycaemia in the treatment of diabetes mellitus" Oxford Textbook of Endocrinology and Diabetes, 2011 pp. 1849-1860.
Choudhary, P., et al., "Insulin Pump Therapy with Automated Insulin Suspension in Response to Hypoglycemia", Diabetes Care, vol. 34, 2011, pp. 2023-2025.
Claims, Specification and Drawings for System and Methods for Providing Sensitive and Specific Alarms, 103 pages.
Clarke, W., et al., "Statistical Tools to Analyze Continuous Glucose Monitor Data", Diabetes Technology & Therapeutics, vol. 11, 2009, pp. S-45-S-54.
Clemens, A.H., et al., "Development of the Biostator® Glucose Clamp Algorithm", Artificial Systems for Insulin Delivery, Serono Symposia Publications from Raven Press, vol. 6, 1983, pp. 399-409.
Close, "Test Driving Dexcom's Short-Term Sensor (STS): A Look at Continuous Glucose Monitoring", diaTribe Learn, Making Sense of Diabetes, 2006, 2 pages.
Continuous Glucose Monitoring (CGM)/Real-Time Flash Glucose Scanning (FGS) Training for Healthcare Professionals and Patients, Association of Children's Diabetes Clinicians, 2017, 50 pages.
Continuous Glucose Sensors: Continuing Questions about Clinical Accuracy, Journal of Diabetes Science and Technology, 2007; 1(5):669-675.
Convolution, Wikipedia, retrieved on May 28, 2016, retrieved from: https://en.wikipedia.org/wiki/Convolution, pp. 1-14.
Cryer, P.E. "Preventing Hypoglycaemia: what is the appropriate glucose alert value?" Diabetologia, 2009, 53:35-37.
Csorgei, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Cunningham, D.D., et al., "In Vivo Glucose Sensing", Wiley, 2010, 466 pages.
Cunningham, D.D., et al., "In Vivo Glucose Sensing", Wiley, 2010, pp. 143-147.
Declaration of Dr. David Rodbard in Support of Petition for Inter Partes Review of Claims 1-5, 12, 19 and 23 of U.S. Pat. No. 10,702,215, Inter Partes Review No. IPR2022-00909 (2022).
Declaration of Duncan Hall (2021) including DexCom™ STS™ Continuous Glucose Monitoring System User's Guide (2006), 64 pages.
Defining and Reporting Hypoglycemia in Diabetes, American Diabetes Association, Diabetes Care, 2005, 28(5):1245-1249.
DeVries, J.H. "Glucose Sensing Issues For the Artificial Pancreas" Journal of Diabetes Science and Technology, 2008, 2(4):732-734.
Dexcom G4 Continuous Glucose Monitoring System, User's Guide, Dexcom, 2013, 156 pages.
Dexcom Request for Confidentiality for FCC ID: PH29433, 1 page (2010).
DexCom™ STS™ Continuous Glucose Monitoring System, User's Guide, 2006, 57 pages.
Diabetes (type 1), PSP Top 10, James, Lind Alliance, Priority Setting Partnerships, 2011, 4 pages.
Diabetes Close Up—Conferences—#2—Diabetes Technology, 8 pages (2003).
Effectiveness and Safety Study of the DexCom™ G4 Continuous Glucose Monitoring System, NIH, U.S. National Library of Medicine, ClinicalTrial.gov, 2010, 4 pages.
El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, vol. 1, No. 2, 2007, pp. 181-192.

(56) References Cited

OTHER PUBLICATIONS

EP Application No. 13859365.2 Extended Search Report dated Jul. 5, 2016.
EP Application No. 18712038.1 Examination Report dated Oct. 12, 2020.
EP Application No. 10812728.3, Examination Report dated Feb. 28, 2018.
EP Application No. 10812728.3, Extended European Search Report dated Aug. 21, 2014.
EP Application No. 20174904, Extended European Search Report dated Sep. 8, 2020.
EP Application No. 21209427.0, Extended European Search Report, dated Mar. 18, 2022.
EP Application No. 21209431.2, Extended European Search Report, dated Mar. 18, 2022.
EP Application No. 22165695.2, Extended European Search Report, dated Sep. 2, 2022, 8 pages.
EP Application No. 22165698.6, Extended European Search Report, dated Sep. 2, 2022, for, 7 pages.
EP Application No. 22165700.0, Extended European Search Report, dated Sep. 2, 2022, 8 pages.
Facchinetti, A., et al., "A New Index to Optimally Design and Compare Continuous Glucose Monitoring Glucose Prediction Algorithms", Diabetes Technology & Therapeutics, vol. 13, No. 2, 2011, pp. 111-119.
Federal Register, vol. 76, No. 120, 2011, pp. 36542-36543.
Federal Register, vol. 86, No. 211, 2021, pp. 60827-60829.
Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Fogt, E.J., et al., "Development and Evaluation of a Glucose Analyzer for a Glucose-Controlled Insulin Infusion System (Biostator®)", Clinical Chemistry, vol. 24, No. 8, 1978, pp. 1366-1372.
FreeStyle Libre 2 Flash Glucose Monitoring System, User's Manual, Abbott, 2021, 141 pages.
FreeStyle Libre 3 Continuous Glucose Monitoring System APP, User's Manual English, Abbott, 2022, 59 pages.
FreeStyle Navigator Continuous Glucose Monitoring System, User Guide, Abbott, 2010, 135 pages.
FreeStyle Navigator II Continuous Glucose Monitoring System, User's Manual, Abbott, 2015, 21 pages.
FreeStyle Navigator, Continuous Glucose Monitoring System, User's Guide, Abbott, 2008, 196 pages.
Frier, B.M. "Defining hypoglycaemia: what level has clinical relevance?", Diabetologia, 2009, 52:31-34.
Garg, S et al., Relationship of Fasting and Hourly Blood Glucose Levels to HbA1c Values, Diabetes Care, 2006, 6(12):2644-2649.
Garg, S., et al., "Improvement in Glycemic Excursions with a Transcutaneous, Real-Time Continuous Glucose Sensor", Diabetes Care, 2006, 29(1):44-50.
Garg, S.K., et al., "Improved Glucose Excursions Using an Implantable Real-Time Continuous Glucose Sensor in Adults with Type1 Diabetes", Diabetes Care, 2004, 27(3):734-738.
Garg, S.K., et al., Diabetes Technology & Therapeutics, 2011, 13(8);15 pages.
GlucoWatch G2, Automatic Glucose Biographer and Autosensors, 2002, 70 pages.
GlucoWatch® G2™ Biographer (GW2B) Alarm Reliability During Hypoglycemia in Children, Diabetes Technol Ther., 6(5): 559-566, 2004, 12 pages.
Gross, T.M., et al., "Performance Evaluation of the MiniMed® Continuous Glucose Monitoring System During Patient Home Use", Diabetes Technology & Therapeutics, vol. 2, No. 1, 2000, pp. 49-56.
Grounds of Invalidity amended pursuant to CPR17.1(2)(a), Claim No. HP-2021-000025, 17 pages (2022).
Guardian® REAL-Time Continuous Glucose Monitoring System, User Guide, Medtronic MiniMed, 2006, 181 pages.
Guerra, S., et al., "A Dynamic Risk Measure from Continuous Glucose Monitoring Data", Diabetes Technology & Therapeutics, vol. 13, No. 8, 2011, pp. 843-852.
Guideline on clinical investigation of medicinal products in the treatment or prevention of diabetes mellitus, European Medicines Agency, May 14, 2012, 28 pages.
Hayter, P.G., et al., "Performance Standards for Continuous Glucose Monitors", Diabetes Technology & Therapeutics, vol. 7, No. 5, 2005, pp. 721-726.
Heinenmann, L., et al., "Glucose Clamps with the Biostator: A Critical Reappraisal", Horm. metab. Res. 26, 1994, pp. 579-583.
Heller, A., "Integrated Medical Feedback Systems for Drug Delivery", AIChE Journal, vol. 51, No. 4, 2005, pp. 1054-1066.
Heller, A., et al., "Electrochemical Glucose Sensors and Their Applications in Diabetes Management", Chemical Reviewes, vol. 108, No. 7, 2008, pp. 2482-2505.
Heller, A., et al., "Electrochemistry in Diabetes Management", Accounts of Chemical Research, vol. 43, No. 7, 2010, pp. 963-973.
Heller, S.R. "Glucose Concentrations of Less Than 3.0 mmol/L (54mg/dL) Should Be Reported in Clinical Trials: A Joint Position Statement of the American Diabetes Association and the European Association for the Study of Diabetes" Diabetes Care, 2017; 40:155-147.
Hermanns, N, et al., "The Impact of Continuous Glucose Monitoring on Low Interstitial Glucose Values and Low Blood Glucose Values Assessed by Point-of-care Blood Glucose Meters: Results of a Crossover Trial", Journal of Diabetes Science and Technology, vol. 8(3), 2014, pp. 516-522.
Instructions for Use DexCom™ STS™ Sensor, 2006, 51 pages.
International Standard, IEC 60601-1-8, Medical Electrical Equipment, 166 pages (2006).
Internet Archive, WayBack Machine, "http://www.minimed.com/doctors/md_products_cgms_ov_completepic.shtml"; Medtronic MiniMed, 2004, 20 pages.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Israeli Patent Application No. 216631, Original Language and English Translation of Official Action dated Sep. 18, 2014.
Javanmardi, C.A., et al., "G4 Platinum Continuous Glucose Monitor", U.S. Pharmacist, The Pharmacist's Resource for Clinical Excellence, 38(9): 64-68, 2013, 8 pages.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Kovatchev, B.P. et al., Assessment of Risk for Severe Hypoglycemia Among Adults With IDDM, Diabetes Care, vol. 21, No. 11, Nov. 1998, pp. 1870-1875.
Kovatchev, B.P., et al., "Evaluating the Accuracy of Continuous Glucose-Monitoring Sensors", Diabetes Care, vol. 27, No. 8, 2004, pp. 1922-1928.
Kovatchev, B.P., et al., "Risk Analysis of Blood Glucose Data: A Quantitative Approach to Optimizing the Control of Insulin Dependent Diabetes", Journal of Theoretical Medicine, vol. 3, 2000, pp. 1-10.
Kovatchev, B.P., et al., "Symmetrization of the Blood Glucose Measurement Scale and Its Applications", Diabetes Care, vol. 20, No. 11, 1997, pp. 1655-1658.

(56) References Cited

OTHER PUBLICATIONS

Letter from Department of Health & Human Services re. MiniMed Continuous Glucose Monitoring System, 7 pages (1999).
Letter from Department of Health and Human Services to Abbott Diabetes Care, Inc. re. FreeStyle Navigator Continuous Glucose Monitoring System, 2008, 7 pages.
Letter to EPO re. Divisional Application of EP Patent Application No. 13784079.9 for Dexcom, Inc. 2020, 2 pages.
Ley, T., Continuous Glucose Monitoring: A Movie is Worth a Thousand Pictures, A Review of the Medtronic Guardian, REAL-time system, 3 pages.
Lortz, J., et al., "What is Bluetooth? We Explain the Newest Short-Range Connectivity Technology", Smart Computing Learning Series, Wireless Computing, vol. 8, Issue 5, 2002, pp. 72-74.
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
McGarraugh, G., et al., "Glucose Measurements Using Blood Extracted from the Forearm and the Finger", TheraSense, Inc., 2001, 16 Pages.
McGarraugh, G., et al., "Physiological Influences on Off-Finger Glucose Testing", Diabetes Technology & Therapeutics, vol. 3, No. 3, 2001, pp. 367-376.
McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
McMurry, "The Artificial Pancreas Today", Henry Ford Hospital Medical Journal, vol. 31, No. 2, Article 4, 1983, pp. 77-83.
Medtronic User Guide Guardian® REAL-Time Continuous Glucose Monitoring System, 2006, 184 pages.
Medtronic, Getting Started with Carelink™ Personal Software For Continuous Glucose Monitoring, 2009.
MiniMed® 530G System User Guide, Medtronic, 317 pages (2012).
National Service Framework for Diabetes: Standards, Dept. of Health, 2002, 48 pages.
Note for Guidance on Clinical Investigation of Medicinal Products in the Treatment of Diabetes Mellitus, The European Agency for the Evaluation of Medicinal Products, 2002, 12 pages.
Oliver, N.S., et al., "Glucose sensors: a review of current and emerging technology", Diabetic Medicine, 2009, 26:197-210.
Original Premarket Approval Application, FreeStyle Navigator Continuous Glucose Monitoring System, Section VII: Manufacturing Section Steven Label Sensor Sheet Validation Plan, vol. 28 of 31, 2005, 61 pages.
OUS Commercialization Agreement between Animas Corporation and DexCom, Inc., 2009, 49 pages.
Palerm, C.C., et al., "Hypoglycemia Detection and Prediction Using Continuous Glucose Monitoring—A Study on Hypoglycemic Clamp Data", Journal of Diabetes Science and Technology, vol. 1, Issue 5, 2007, pp. 624-629.
PCT Application No. PCT/US2018/020030 ISR and Written Opinion dated May 9, 2018.
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pickup, J.C. "Glucose monitoring", Oxford Textbook of Endocrinology and Diabetes, 2011, pp. 1861-1869.
Pickup, J.C. et al., "Glycaemic control in type 1 diabetes during real time continuous glucose monitoring compared with self monitoring of blood glucose: meta-analysis of randomised controlled trials using individual patient data" BMJ, 2011; 14 pages.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Premarket Approval (PMA), U.S. Food & Drug Administration, Biostator GCIIS, Notice Date: 1981, 3 pages.
Premarket Approval (PMA), U.S. Food & Drug Administration, Continuous Glucose Monitoring System, Notice Date: 1999, 20 pages.
Premarket Approval (PMA), U.S. Food & Drug Administration, Dexcom Seven Plus System, 2009, 3 pages.
Premarket Approval (PMA), U.S. Food & Drug Administration, Dexcom STS Continuous Monitors, Notice Date: 2006, 8 pages.
Premarket Approval (PMA), U.S. Food & Drug Administration, FreeStyle Navigator Continuous Glucose Monitor, Notice Date: 2008, 6 pages.
Premarket Approval Application Amendment, FreeStyle Navigator Continuous Glucose Monitoring System, vol. 2 of 39, Section III, Device Description, 2006, 89 pages.
Press Release Details, DexCom Receives FDA Approval for STS™ Continuous Glucose Monitoring System, 3 pages (2006).
Puhr, S et al., "Real-World Hypoglycemia Avoidance with a Predictive Low Glucose Alert Does Not Depend on Frequent Screen Views", Journal of Diabetes Sciences and Technology, 2004, 14(1): 83-86.
Quinn, C. P., et al., "Kinetics of Glucose Delivery to Subcutaneous Tissue in Rats Measured with 0.3-mm Amperometric Microsensors", The American Physiological Society, 1995, E155-E161.
Rilestone, S et al., "The impact of CGM with a predictive hypoglycaemia alert function on hypoglycaemia in physical activity for people with type 1 diabetes: PACE study", Dexcom, 2022, 2 pages.
Rodbard, D., "A Semilogarithmic Scale for Glucose Provides a Balanced View of Hyperglycemia and Hypoglycemia", Journal of Diabetes Science and Technology, vol. 3, Issue 6, 2009, pp. 1395-1401.
Roe, J. N., et al., "Bloodless Glucose Measurements", Critical Review in Therapeutic Drug Carrier Systems, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidtke, D. W., et al., "Measurement and Modeling of the Khsient Difference Between Blood and Subcutaneous Glucose Concentrations in the Rat After Injection of Insulin", Proceedings of the National Academy of Sciences, vol. 95, 1998, pp. 294-299.
Seven Steps to Start, The DexCom's SEVEN® PLUS Quick Start Guide, 2010, 2 pages.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.

(56) References Cited

OTHER PUBLICATIONS

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.
Standards of Medical Care in Diabetes—2009, Position Statement, American Diabetes Association, 2009, Diabetes Care, 32(1):S13-S61.
Sternberg, R., et al., "Study and Development of Multilayer Needle-Type Enzyme-Based Glucose Microsensors", Biosensors, vol. 4, 1988, pp. 27-40.
STS® Seven Continuous Glucose Monitoring System, User's Guide, 2007, 74 pages.
Summary of Safety and Effectiveness Data, DexCom™ STS™ Continuous Glucose Monitoring System, 2006, 20 pages.
Summary of Safety and Effectiveness Data, FreeStyle Navigator® Continuous Glucose Monitoring System, 2008, 27 pages.
Summary of Safety and Effectiveness Data, STS®-7 Continuous Glucose Monitoring System, 2007, 14 pages.
Swinnen, S.G.H.A. et al., "Changing the glucose cut-off values that define Hypoglycaemia has a major effect on reported frequencies of hypoglycaemia", Diabetologia, 2009, 52:3 8-41.
Teller, "A platform for wearable physiological computing," Interacting with Computers 16:917-937 (2004).
The Effect of Intensive Treatment of Diabetes on the Development and Progression of Long-Term Complications in Insulin-Dependent Diabetes Mellitus, The New Journal of Medicine, 1993, 329(14):977-986.
TheraSense Files Premarket Approval Application for Freestyle Navigator(TM) Cont, 2003, 3 pages.
Therasense Navigates Continuous Glucose Monitor PMA, Prepares for Flash, the Gray Sheet, vol. 29, No. 3 7, 2003, 2 pages.
Thompson, M., et al., "In Vivo Probes: Problems and Perspectives", Clinical Biochemistry, vol. 19, 1986, pp. 255-261.
Turner, A., et al., "Diabetes Mellitus: Biosensors for Research and Management", Biosensors, vol. 1, 1985, pp. 85-115.
Type 1 Diabetes Research Roadmap, "Identifying the strengths and weaknesses, gaps and opportunities of UK type 1 diabetes research; clearing a path to cure" , Type 1 diabetes research roadmap, JDRF, 2013, 21 pages.
Type 1 diabetes: diagnosis and management of type 1 diabetes in children, young people and adults, National Institute for Clinical Excellence, Clinical Guideline 15, Jul. 2004, 113 pages.
United States Securities and Exchange Commission, Form 10-K, DexCom, Inc., 2006, 59 pages.
United States Securities and Exchange Commission, Form 10-K, DexCom, Inc., 2007, 55 pages.
United States Securities and Exchange Commission, Form S-1, Dexcom, Inc., 309 pages (2005).
U.S. Appl. No. 15/199,765, Office Action dated Apr. 5, 2018.
U.S. Appl. No. 15/260,288, Office Action dated Jun. 27, 2017.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Velho, G., et al., "Strategies for Calibrating a Subcutaneous Glucose Sensor", Biomedica Biochimica Acta, vol. 48, 1989, pp. 957-964.
Welcome to Your FreeStyle Libre System In-Service Guide, FreeStyle Libre, Flash Glucose Monitoring System, Abbott, 2017, 22 pages.
Wiliams, S., et al., "The Guardian REAL-Time Continuous Glucose Monitoring System", U.S. Pharmacist, The Pharmacist's Resource for Clinical Excellence, 2007, 16 pages.
Williamson et al., "Data Sensing and Analysis: Challenges for Wearables," The 20th Asia and South Pacific Design Automation Conference, IEEE, 2015, pp. 136-141.
Wilson, G. S., et al., "Progress Toward the Development of an Implantable Sensor for Glucose", Clinical Chemistry, vol. 38, No. 9, 1992, pp. 1613-1617.
U.S. Appl. No. 17/720,986, (US 2022-0233111 A1), filed Apr. 14, 2022 (Jul. 28, 2022).
U.S. Appl. No. 17/720,986, Nov. 15, 2022 Request for Continued Examination.
U.S. Appl. No. 17/720,986, Sep. 23, 2022 Notice of Allowance.
U.S. Appl. No. 14/720, 986, Sep. 13, 2022 Response to Non-Final Office Actoin.
U.S. Appl. No. 17/720,986, Jun. 13, 2022 Non-Final Office Action.
Hanlon, M. "Dexcom's 7 Day STS Continuous Glucose Monitoring System" Health & WellBeing, 2007 (1 page).
Exhibit No. 22, to the Expert Report of Professor Nick Oliver, Sep. 20, 2022: Innovation Milestones, et al.
Kamath, A et al., "Method of Evaluating the Utility of Continuous Glucose Monitor Alerts", Journal of Diabetes Science and Technology, 2010, vol. 4, Issue 1, pp. 57-66.
FDA PMA Approvals—EP2914159, 3 pages. Downloaded Sep. 14, 2022.
Feature Analysis, 1 page, Mar. 9, 2022.
FreeStyle Navigator, Continuous Glucose Monitoring System, User's Guide, 38 pages. (2008).
Piezoelectric accelerometer, retrieved from https://en.wikipedia.org/wiki/ Piezoelectric_accelerometer, pp. 1-4. (Sep. 29, 2022).
Sandham et al., "Blood Glucose Prediction for Diabetes Therapy Using Recurrent Artificial Neural Network," 9th European Signal Processing Conference (EUSIPCO 1998), IEEE (1998).
The CGM Resource Center References/Bibliography, 14 pages. (Jun. 12, 2011).
Alva et al., "Accuracy of a 14-Day Factory-Calibrated Continuous Glucose Monitoring System with Advanced Algorithm in Pediatric and Adult Population with Diabetes," Journal of Diabetes Science and Technology, vol. 16(1) 70-77 (2022).
Campbell et al., "Outcomes of using flash glucose monitoring technology by children and young people with type 1 diabetes in a single arm study," Pediatric Diabetes, 1294-1301 (2018).
Deshmuk et al., "Effect of Flash Glucose Monitoring on Glycemic Control, Hypoglycemia, Diabetes-Related Distress, and Resource Utilization in the Association of British Clinical Diabetologists (ABCD) Nationwide Audit," https://doi.org/10.2337/dc20-0738, Diabetes Care, 8 pages (2020).
Deutscher Gesundheitsbericht, Diabetes 2021, Die Bestandsaufnahme , German Diabetes Society, with English Abstract, 15 pages (2021).
Haak et al., "Use of Flash Glucose-Sensing Technology for 12 months as a Replacement for Blood Glucose Monitoring in Insulin-treated Type 2 Diabetes," Diabetes Ther., 14 pages (2017).
Letter from Department of Health & Human Services, Food and Drug Administration, to Andy Balo, DexCom, Inc. re. P050012/S001, STS-7 Continuous Glucose Monitoring System dated May 31, 2007, 95 pages.
Roussel et al., "Important Drop in Rate of Acute Diabetes Complications in People With Type 1 or Type 2 Diabetes After Initiation of Flash Glucose Monitoring in France: The RELIEF Study," American Diabetes Association, Diabetes Care, 1368-1376 (2021).
Premarket Approval Letter with Summary of Safety and Effectiveness Data for the Freestyle Navigator Continuous Glucose Monitor, Mar. 12, 2008 [ 34 pgs.].
User Guide for the Navigator Freestyle (Mar. 2008) [38 pgs.].
File history of U.S. Appl. No. 61/551,773, filed Oct. 26, 2011.
Harvey, et al., Clinically Relevant Hypoglycemia Prediction Metrics for Event Mitigation, Diabetes Technology & Therapeutics, vol. 14, No. 8, pp. 719-727 (2012).
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, Issue 5, pp. 1146-1155 (2010).
Schiavon, An online method for prevention of the risk of glycemic shock in diabetic patients from continuous glucose monitoring data, 117 pages (2010) with English translation of summary attached.
Hughes, et al., Hypoglycemia Prevention via Pump Attenuation and Red-Yellow-Green "Traffic" Lights Using Continuous Glucose Moni-

(56) References Cited

OTHER PUBLICATIONS toring and Insulin Pump Data, Journal of Diabetes Science and Technology, vol. 4, No. 5, pp. 1146-1155 (2010).
Schiavon, A method online for there prevention of the risk of glycerine shock in diabetic patients from data of monitoring continuous of the glucose [with English translation], 220 pages (2010).
Townsend, et al., Getting Started with Bluetooth Low Energy, Tools and Techniques for Low-Power Networking, O'Reilly, 180 pages (2014).
Wang, et al., NYIT School of Engineering and Computing Sciences, A Feasible IMD Communication Protocol: Security without Obscurity, 1 page (2015).
Approval letter from Department of Health and Human Services re. P050012/S001, STS-7 Continuous Glucose Monitoring System, dated May 31, 2007, 7 pages.
Ballard, "User Interface Design Guidelines for J2ME MIDP 2.0" 9 pages (2005).
Certified Copy of U.S. Appl. No. 61/238,657, filed Aug. 31, 2009, 60 pages.
Certified Copy of U.S. Appl. No. 61/238,657, filed Aug. 31, 2009, 198 pages.
Certified Copy of U.S. Appl. No. 61/247,541, filed Sep. 30, 2009, 69 pages.
Certified Copy of U.S. Appl. No. 61/297,265, filed Jan. 22, 2010, 54 pages.
Cunningham et al., Winefordner Seried Editor, "Chemical Analysis: A Seried of Monographs on Analytical Chemistry and Its Applications—In Vivo Glucose Sensing" 50 pages (2010).
Declaration of Thomas Edward Foster of Taylor Wessing LLP, Hill House, 1 Little New St. London EC4A 3TR ("Taylor Wessing"), in Relation to STS-7 User's Guide, Jan. 30, 2024, 160 pages.
FDA Premarket Approval PMA Order for the STS-7, 3 pages, May 31, 2007.
Freestyle Navigator CGSM Users Guide, 196 pages (2008).
File History of U.S. Pat. No. 10,375,222, issued Aug. 6, 2019, 442 pages.
Microsoft Applications for Windows Mobile 6 User Guide, 184 pages (2008).
NFC Forum, Bluetooth® Secure Simple Pairing Using NFC Application Document NFC ForumTM, NFCForum-AD-BTSSP 1_1, Jan. 9, 2014, 39 pages.
Omre, Bluetooth Low Energy: Wireless Connectivity for Medical Monitoring, Journal of Diabetes Science and Technology, vol. 4, Issue 2, 457-463 Mar. 2010.
Padgette et al., "Guide to Bluetooth Security, Recommendations of the National Institute of Standards and Technology," National Institute of Standards and Technology, U.S. Department of Commerce, Special Publication 800-121 Revision 1, 48 pages, May 2007.
PMA Final Decisions Rendered for May 2007, The Wayback Machine, U.S. Food and Drug Administration, 21 pages.
Specification Bluetooth System Experience More, 134 pages, Jun. 2010.
Specification Bluetooth System Wireless connections, 92 pages, Nov. 2003.
Strömmer et al., "Application of Near Field Communication for Health Monitoring in Daily Life," Proceedings of the 28th IEEE FrC09.1 EMBS Annual International Conference New York City, USA, 3246-3249, Aug. 30-Sep. 3, 2006.
STS® Seven Glucose Monitoring System User's Guide, 74 pages (2007).
STS-7 Continuous Glucose Monitoring System—P050012/S001, Approved May 31, 2007, The Wayback Machine, U.S. Food and Drug Administration, 1 page.
Zhang et al., "Bluetooth Low Energy for Wearable Sensor-based Healthcare Systems," 2014 Health Innovations and Point-of-Care Technologies Conference Seattle, Washington USA, 251-254, Oct. 8-10, 2014.
Approved Judgment, In the High Court of Justice Business and Property Courts of England and Wales Intellectual Property List (ChD) Patents Court, Case No. HP-2021-000025 & HP-2021-000026, 137 pages, Jan. 15, 2024.
Bequette, "Continuous Glucose Monitoring: Real-Time Algorithms for Calibration, Filtering, and Alarms," Journal of Diabetes Science and Technology, vol. 4, Issue 2, 404- 418, Mar. 2010.
Breen, The iPhone Pocket Guide, Sixth Edition, Peachpit Press, 96 pages (2012).
Dassau et al., Real-Time Hypoglycemia Prediction Suite Using Continuous Glucose Monitoring, A safety net for the artificial pancreas, Diabetes Care, vol. 33, No. 3, 1249-1254 (2010).
Declaration of Dr. Sayfe Kiael, Ph.D., Inter Partes Review of U.S. Pat. No. 10,375,222, 100 pages (2024).
Declaration of David Rodbard, M.D., Petition for Inter Partes Review of U.S. Pat. No. 9,119,528, IPR2024-00840, 109 pages, May 1, 2024.
Declaration of Lane Desborough, Petition for Inter Partes Review of U.S. Pat. No. 11,213,204, IPR2024-00853, 150 pages, May 3, 2024.
Declaration of Sylvia D. Hall-Ellis, Ph.D., IPR2024-00840 of U.S. Pat. No. 9,119,528, Parts 1-2 (400 pages) Apr. 24, 2024.
Department of Health & Human Services, FDA, P050012/S001, STS-7 Continuous Glucose Monitoring System, 7 pages, May 31, 2007.
Desalvo et al., "Remote Glucose Monitoring in Camp Setting Reduces the Risk of Prolonged Nocturnal Hypoglycemia," Diabetes Technology & Therapeutics, vol. 16, No. 1, 10 pages, DOI: 10.1089/dia.2013.0139 (2014).
Dexcom, Leading the Way for You & Your Patients with Continuous Glucose Monitoring, 12 pages (2010).
FDA [Docket No. FDA-2011-D-0464], Draft Guidance for Industry and Food and Drug Administration Staff: The Content of Investigational Device Exemption and Premarket Approval Applications for Low Glucose Suspend Device Systems; Availability, Federal Register / vol. 76, No. 120 / Wednesday, Jun. 22, 2011 /Notices, 2 pages.
FDA Premarket Approval (PMA) for Seven Plus Continuous Glucose Monitoring System, Notice Date: Jun. 28, 2007, 3 pages.
FDA Premarket Approval (PMA), Seven Plus Continuous Glucose Monitoring System, https://www.accessdata.fda.gov/scripts/cdrh/cfdocs/cfpma/pma.cfm?id=P050012S001, 3 pages, May 31, 2007.
FDA PMA Final Decisions Rendered for May 2007—The Wayback Machine—https://web.archive.org/web/20070630150626/http:/www.fda.gov/cdrh/pma/pmamay07.html, 21 pages, May 31, 2007.
FDA STS-7, Glucose Monitoring System—P050012/S001, The Wayback Machine—https://web.archive.org/web/20070705190828/http:/www.fda.gov:80/cdrh/pdf5/p050012s001.html, 1 page, 2007.
FDA FreeStyle Navigator Continuous Glucose Monitoring System, P050020, 7 pages, Mar. 12, 2008.
Federal Register, vol. 76, No. 120, Jun. 22, 2011, pp. 36542-36543.
File History of U.S. Pat. No. 9,119,528 issued Sep. 1, 2015, Parts 1-8 (1,438 pages).
File History of U.S. Pat. No. 9,801,541 issued Oct. 31, 2017, 834 pages.
File History of U.S. Pat. No. 11,213,204 issued Jan. 1, 2022, 848 pages.
Facchinetti et al., "A New Index to Optimally Design and Compare Continuous Glucose Monitoring Glucose Prediction Algorithms," Diabetes Technology & Therapeutics, vol. 13, No. 2, 111-119 (2011).
Freestyle Navigator Continuous Glucose Monitoring System, User's Guide, 195 pages (2008).
Hon, Urging FDA to Act Promptly to Approve Artificial Pancreas Technologies, Congressional Record (Bound Edition), vol. 157 (2011), Part 13, 3 pages.
Keith-Hynes et al., "The Diabetes Assistant: A Smartphone-Based System for Real-Time Control of Blood Glucose," Electronics, 3, 609-623; doi:10.3390/electronics3040609 (2014).
Klonoff et al., "Innovations in Technology for the Treatment of Diabetes: Clinical Development of the Artificial Pancreas (an Autonomous System)," Journal of Diabetes Science and Technology, vol. 5, Issue 3, 804-826, May 2011.
Kowalski, "Can We Really Close the Loop and How Soon? Accelerating the Availability of an Artificial Pancreas: A Roadmap to

(56) References Cited

OTHER PUBLICATIONS

Better Diabetes Outcomes," Diabetes Technology & Therapeutics, vol. 11, Suppl 1, DOI: 10.1089/dia.2009.0031, S-113-S-119, 10 pages (2009).
Ley, "Continuous Glucose Monitoring: A Movie is Worth a Thousand Pictures A Review of the Medtronic Guardian REAL-time system," https://nfb.org/images/nfb/publications/vod/vod_22_4/vodfal0702.htm, 3 pages (2021).
McDaniel et al., "Remote Management of Cardiac Patients, The Forefront of a New Standard," Modern Healthcare, 6 pages, Nov. 14, 2011.
Murphy et al., "Closed-Loop Insulin Delivery During Pregnancy complicated by Type 1 Diabetes," Emerging Treatments and Technologies, Diabetes Care, vol. 34, 406-411 (2011).
mySentry™M User Guide, Medronic Minimed, 80 pages (2010).
Padgette et al., "Guide to Bluetooth Security, Recommendations of the National Institute of Standards and Technology," NET Special Publication 800421 Revision National Institute of Standards and Technology, U.S. Department of Commerce, 48 pages (2012).
Palerm et al., "Hypoglycemia Prediction and Detection Using Optimal Estimation," Diabetes Technology & Therapeutics, vol. 7, No. 1, 12 pages (2005).
Pickup, "Semi-Closed-Loop Insulin Delivery Systems: Early Experience with Low- Glucose Insulin Suspend Pumps," Diabetes Technology & Therapeutics, vol. 13, No. 7, DOI: 10.1089/dia.2011.0103, 695-698 (2011).
Place et al., "DiAs Web Monitoring: A Real-Time Remote Monitoring System Designed for Artificial Pancreas Outpatient Trials," Journal of Diabetes Science and Technology vol. 7, Issue 6, 1427-1435 (2013).
Scheduling Order, *Abbott Diabetes Care Inc v. Dexcom, Inc.*, C.A. No. 23-239 (KAJ), 14 pages, Sep. 19, 2023.
Schiavon, "A method online For there prevention of the risk of glycerine shock in diabetic patients from data Of rmonitoring continuous of the glucose," Thesis (with English translation) 219 pages, Apr. 20, 2010.
Steil et al., "Feasibility of Automating Insulin Delivery for the Treatment of Type 1 Diabetes," Diabetes, vol. 55, 3344-3350 (2006).
Strömmer et al., "Application of Near Field Communication for Health Monitoring in Daily Life," Proceedings of the 28th IEEE FrC09., EMBS Annual International Conference, 3246-3249, Aug. 30-Sep. 3, 2006.
The Diabetes Research in Children Network (DirecNet) Study Group, "GlucoWatch® G2TM Biographer (GW2B) Alarm Reliability During Hypoglycemia in Children*," Diabetes Technol Ther., 6(5): 559-566 (2004).
Weinstein et al., "Diabetes Care, ADA 2006: Spotlight on Continuous Glucose Monitoring," JP Morgan, North America Equity Research, 16 pages, Jun. 11, 2006.
Weinzimer et al., "Fully Automated Closed-Loop Insulin Delivery Versus Semiautomated Hybrid Control in Pediatric Patients with Type 1 Diabetes Using an Artificial Pancreas," Emerging Treatments and Technologies, Diabetes Care, vol. 31, No. 5, 934-939 (2008).
Wettlaufer, "Merlin.Net Automation of External Reports Verification Process," A Thesis Presented to The Faculty of California Polytechnic State University, San Luis Obispo, 53 pages, Jan. 2010.
Wilson et al., "Introduction to the Glucose Sensing Problem," In Vivo Glucose Sensing, Edited by D. D. Cunningham and J. A. Stenken, Wiley & Sons, Inc., 27 pages (2010).
Wright et al., "Continuous Glucose Monitoring (CGM)/Real-Time Flash Glucose Scanning (FGS) Training for Healthcare Professionals and Patients," Association of Children's Diabetes Clinicians, 50 pages (2017).
A Dictionary of Computer Science, Seventh Edition, Oxford University Press, "authentication", 3 pages (2016).
A Dictionary of Computing, Sixth Edition, Oxford University Press, "function", 3 pages (2008).
Ananthi, "A Text Book of Medical Instruments," New Age International (P) Limited, Publishers, 7 pages (2005).
Annex A2 Documents relating to the Patent Extract from the EP Register for the Patent, EP 3988471, 6 pages (2023).
Annex B1 Evidence relating to infringing products Dexcom G6 Start Here Guide, 21 pages (2023).
Annex B3 User Guide LibreLinkUp, 28 pages (2023).
Annex B4 Extract from the pricacy notice for Libre View, 7 pages (2024).
Annex C1 Evidence relating to infringing acts Materials concerning supply of Dexcom's Products in France, 10 pages (2022).
Annex Di Upc Court of Appeal Feb. 26, 2024, 335/2023, 38 pages (2024).
Annex D38 Info Technology Digest, vol. 5 Issue 5, 32 pages (1996).
Annex D39 Best Practice for Software Asset Management, 7 pages (2023).
Annex D40 Nagpal, "Computer Fundamentals, concepts, Systems and Applications," 5 pages (2008).
Annex D45 Cunningham, In Vivo Glucose Sensing, 9 pages (2010).
Annex E3 Excerpts from the "German Health Report Diabetes 2023" of the German Diabetes Society, 23 pages (2023) with English translation.
Annex F5 Application to amend the Patent under R30 RoP, 5 pages (2024).
Annex G2 Case law of the Boards of Appeal, I.C-4.3, 3 pages (2024).
Annex G3 European Patent Guide, 23rd ed., chapter 3 ("Patentability"), 3.4, 6 pages (2023).
Annex G5 Case Law of the Boards of Appeal, I-D, 4.2.0, 2 pages (2023).
Annex G6 UPC Court of Appeal Feb. 26, 2024 *NanoString Technologies v. 10x Genomics*, 38 pages (2024).
Annex G7 Decision of the Enlarged Board of the EPO, G 3/14 97 pages (2015).
Annex G8 Willem Hoyng, "The Unified Patent Court (UPC) opens its doors! Some observations", 42 pages (2023).
Annex G10 Düsseldorf Local Division Oct. 18, 2023, UPC_CFI 177 2023 (*MyStromer v Revolt Zycling*), 19 pages (2023).
Annex G11 Munich Local Division Apr. 23, 2024, UPC CFI 514/2023 (*Volkswagen AG, Audi AG, Texas Instruments Inc. and Texas Instruments Deutschland GmbH v. Network system Technologies LLC*), 10 pages (2024).
Annex G12 Munich Local Division, Sep. 19, 2023, UPC_CFI_2/2023 (*NanoString Technologies v. 10x Genomics*), 107 pages (2023).
Annex G13 Regulation 2017/745 (EU), 176 pages (2017).
Annex G14 P. England, 'A Practitioner's Guide to the Unified Patent Court and Unitary Patent', Hart Publishing 2022, p. 159, 7 pages (2022).
"Biomedical Engineering Desk Reference," Elsevier, 5 pages (2009).
Burr et al., Electronic Authentication Guideline, NIST Special Publication 800-63-2, Nist U.S. Dept. of Commerce, Aug. 2013, 123 pages.
Cunningham et al., "In Vivo Glucose Sensing," Wiley & Sons, 50 pages (2010).
Cunningham et al., "In Vivo Glucose Sensing," Wiley & Sons, 111 pages (2010).
Cunningham et al., "In Vivo Glucose Sensing Chemical Analysis: A Series of Monographs on Analytical chemistry and Its Applications," Wiley & Sons, 1 page (2010).
Custodio et al., "A Review on Architectures and Communications Technologies for Wearable Health-Monitoring Systems," Sensors 12, 13907-13946 (2012).
D26 Microsoft Applications for Windows Moblie 6, User Guide, Part 1 92 pages, Part 2 92 pages (2008).
D29 Medtronic, Paradigm REAL-Time Revel™M Minimed, Part 1 132 pages, Part 2 133 pages (2009).
Dexcom, Seven Plus CGMS Users Guide, Part 1, 72 pages, Part 2, 72 pages (2008).
D'Imporzano, Dr., "Reaching More of the World," Johnson & Johnson Celebrating 125 Years, Annual Report 2010, 2 pages.
Ericksen et al., "Orthospinology Procedures, An Evidence-Based Approach to Spinal Care," 6 pages (2007).

(56) References Cited

OTHER PUBLICATIONS

FreeStyle Navigator® CGMS Indications for Use, 96 pages (2008).
G7 User Guide, Instructions for Use, 174 pages (2024).
"GlucoWatch® G2™M Biographer (GW2B) Alarm Reliability During Hypoglycemia in Children," Diabetes Technol Thee., 6(5): 559-566, 12 pages (Oct. 2004).
Hashimoto et al., "Examination of Usefulness of Color Indicator Function of OneTouch Ultra VueTM, Medicine and Pharmacy," D44-D43, Opposition EP 3 988 471 B1, Hoffmann Elite, 9 pages (with English Translation) (2010).
Huizinga et al., "Automated Defect Prevention, Best Practices in Software Management," 6 pages (2007).
IEEE 100 The Authoritative Dictionary of IEEE Standards Terms, Seventh Ed., "authentication", 3 pages (2000).
Letter to Bob Shen at Dexcom, Inc. dated May 15, 2023, FDA U.S. Food & Drug Administration, 8 pages.
Medronic, The MiniMed Paradigm® REAL-Time System, 8 pages (2005).
Medronic, Guardian REAL-Time, User Guide CGMS, 181 pages (2006).
Medronic, The MiniMed Paradigm® REAL-Time System, Insulin Pump and CGMS, 8 pages (2008).
Medronic, The MiniMed Paradigm® REAL-Time Insulin Pump User Guide, Paradigm® 522 and 722 Insulin Pumps, 176 pages (2006).
Medronic, Guardian® REAL-Time Continuous Glucose Monitoring System, User Guide, 184 pages (2006).
Medronic, The MiniMed Paradigm® REAL-Time Sensor Features User Guide, Paradigm® 522 and 722 Insulin Pumps, 76 pages (2006).
Medronic, Paradigm® REAL-Time. Revel IM Insulin PumpUser Guide, 132 pages (2009).
Mosa et al., "A Systematic Review of Healthcare Applications for Smartphones," BMC Med Informatice and Secision Making, 32 pages (2012).
Motorola, Microsoft Applications for Windows Mobile 6 User Guide, 184 pages (2008).
Newton, Newton's Telecom Dictionary, 30th Upldated, Expanded, Aniversry Ed., "authenticate", 4 pages (2016).
OneTouch Handling Instructions, For self-examination glucose meter, Part 1-36 pages, Part 2-36 pages, Part 3-36 pages (with English Translation 6 pages) (2018).
OneTouch Ultra VueTM, 3 pages (2010).
Section 7 Calibrate Your System/Test Blood Glucose Manually, 65 pages (2008).
Section 10 Response to Alarms, Errors, and Problems, 96 pages (2008).
Seven Plus continuous glucose monitoring system User's Guide, Dexcom, 72 pages (2008).
Seven Plus Glucose Monitoring System Users Guide, Dexcom, 144 pages (2008).
Sommerville, "Software Engineering," 7 pages (2007).
Stone et al., "User Interface Design and Evaluation," The Open University, 4 pages (2005).
Stone et al., "User Interface Design and Evaluation," The Open University, 13 pages (2005).
Stone et al., "User Interface Design and Evaluation," The Open University, 153 pages (2005).
Stoodley et al., "The Automatic Detection of Transients, Step Changes and Slope Changes in the Monitoring of Medical Time Series," The Statistician, vol. 28 No. 3, 163-170 (1979).
Wiklund, "Medical Device and Equipment Design," 6 pages (1995).
Select pages from OneTouch Ultra Vue User Manual published on Oct. 1, 2009 (with English Translation), 4 pages.

\* cited by examiner

CONTINUOUS GLUCOSE MONITORING SYSTEM

CROSS-REFERENCE TO RELATED APPLICATIONS

The present application is a continuation of U.S. patent application Ser. No. 17/567,684, filed Jan. 3, 2022, which is a continuation of U.S. patent application Ser. No. 16/560,497, filed Sep. 4, 2019, now U.S. Pat. No. 11,213,622 which is a continuation of U.S. patent application Ser. No. 15/282,688 filed on Sep. 30, 2016, which is a divisional of U.S. patent application Ser. No. 14/076,109, filed Nov. 8, 2013, which is a continuation of U.S. patent application Ser. No. 12/785,144, filed May 21, 2010, now U.S. Pat. No. 8,597,274, which claims the benefit of U.S. Provisional Appl. No. 61/180,649, filed May 22, 2009, all of which are incorporated herein by reference in their entireties for all purposes.

This application is also related to U.S. application Ser. No. 12/784,981, filed May 21, 2010, entitled "Methods For Reducing False Hypoglycemia Alarm Occurrence," and now U.S. Pat. No. 9,579,456 (U.S. Provisional No. 61/180,700, filed May 22, 2009); U.S. application Ser. No. 12/785,104, filed May 21, 2010, now U.S. Pat. No. 8,257,300, issued Sep. 4, 2012, entitled "Safety Features For Integrated Insulin Delivery System," (U.S. Provisional Application No. 61/180,627, filed May 22, 2009); U.S. application Ser. No. 12/785,096, filed May 21, 2010, now U.S. Pat. No. 8,398,616, issued May 19, 2013, entitled "Safety Layer For Integrated Insulin Delivery System," (U.S. Provisional Application No. 61/180,774, filed May 22, 2009); and U.S. application Ser. No. 12/785,196, filed May 21, 2010, entitled "Adaptive Insulin Delivery System," now abandoned (U.S. Provisional Application No. 61/180,767, filed May 22, 2009).

BACKGROUND

Diabetes is a metabolic disorder that afflicts tens of millions of people throughout the world. Diabetes results from the inability of the body to properly utilize and metabolize carbohydrates, particularly glucose. Normally, the finely tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In persons with insulin-dependent diabetes, the symptoms of the disease can be controlled by administering additional insulin (or other agents that have similar effects) by injection or by external or implantable insulin pumps. The "correct" insulin dosage is a function of the level of glucose in the blood. Ideally, insulin administration should be continuously readjusted in response to changes in glucose level.

Presently, systems are available for continuously monitoring a person's glucose levels by implanting a glucose sensitive probe into the person. Such probes measure various properties of blood or other tissues, including optical absorption, electrochemical potential and enzymatic products. The output of such sensors can be communicated to a hand held device or controller that is used to calculate an appropriate dosage of insulin to be delivered to the user of the continuous glucose monitor (CGM) in view of several factors, such as the user's present glucose level, insulin usage rate, carbohydrates consumed or to be consumed and exercise, among others. These calculations can then be used to control a pump that delivers the insulin, either at a controlled "basal" rate, or as a "bolus" into the user. When provided as an integrated system, the continuous glucose monitor, controller and pump work together to provide continuous glucose monitoring and insulin pump control.

Such systems can be closed loop systems, where the amount of insulin being delivered is completely controlled by the controller and pump in conjunction with glucose level data received from the CGM device. Alternatively, such systems may be open loop systems, where the user evaluates the glucose level information from a glucose monitoring device and then instructs the pump accordingly, or the system may be a semi-closed loop system that combines various aspects of a closed loop and open loop system.

Typically, present systems may be considered to be open or semi-closed loop in that they require intervention by a user to calculate and control the amount of insulin to be delivered. However, there may be periods when the user is not able to adjust insulin delivery. For example, when the user is sleeping, he or she cannot intervene in the delivery of insulin, yet control of a patient's glucose level is still necessary. A system capable of integrating and automating the functions of glucose monitoring and controlled insulin delivery into a closed loop system would be useful in assisting users in maintaining their glucose levels, especially during periods of the day when they are unable or unwilling to the required calculations to adjust insulin deliver to control their glucose level.

What has been needed, and heretofore unavailable, is an integrated, automated system combining continuous glucose monitoring and controlled insulin delivery. Such a system would include various features to insure the accuracy of the glucose monitor and to protect the user from either under- or over-dosage of insulin. The system would include various functions for improving the usability, control, and safety of the system, including a variety of alarms which could be set by a user or a technician to avoid false alarms while ensuring adequate sensitivity to protect the user. The present invention satisfies these and other needs.

SUMMARY OF THE INVENTION

Briefly, and in general terms, the invention is directed to new and improved systems and methods for management of a user's glucose level, including systems and methods for improving the usability and safety of such systems including continuous glucose monitors and a drug delivery pumps.

In one aspect, the invention is directed to a system and method for use when insulin delivery is to be restarted after an unexpected stop in delivery. In this aspect of the invention, insulin history and glucose level history are used for calculating and recommending a bolus volume of insulin to be delivered to bring a user's insulin on board, that is, residual insulin that is unmetabolised and circulating in the user's blood stream since insulin was last added, up to the level it would have been had insulin delivery not been stopped.

In another aspect, a safe amount and duration of basal rate insulin delivery is determined using model-based calculation of insulin on board, past insulin delivery information, past and present glucose information of the user and a predicted glucose profile over a near-future time horizon, among other factors, in the event that a closed loop insulin delivery system terminates closed loop operation unexpectedly.

In still another aspect, the invention includes a system and method for enhancing alarm avoidance with pre-emptive pump control command modification, which is advantageous when compared with simply muting an alarm, and is less annoying than a persistent projected low glucose alarm. In yet another aspect, a user interface is provided that integrates and cooperates with the enhanced alarm avoidance system and method to facilitate use of the system.

In a further aspect, a system and method is included that is directed to reducing the frequency of false low glucose alarms, particularly when an insulin delivery system is operating in a closed loop mode, by allowing for the possibility of the complete or partial recovery from an artifact, such as a sensor drop out, to occur prior to an alarm presentation to a user of the system.

In another aspect, a model-based calculation of the present and near-future values of best estimate and upper/lower bounds of glucose is made to adjust a tiered alarm mechanism in order to account for predicted hypoglycemic and hyperglycemic events.

In yet another aspect, the invention includes a method for determining a bolus volume to be administered to make up for a cessation of basal delivery of insulin, comprising: determining an amount of insulin remaining in a user's body such that insulin remaining=amount of insulin delivered before cessation×(user's insulin action time minus the time since insulin was last delivered)/(user's insulin action time); and calculating a bolus delivery to equal the amount of basal delivery lost. In another aspect, determining an amount of insulin remaining includes using a model to estimate the amount of insulin remaining.

In still another aspect, the invention includes a method of determining an insulin delivery rate when a closed loop insulin delivery system terminates unexpectedly, comprising: a) providing a glucose level and predicting a future glucose level in order to determine the appropriate insulin bolus for the latest control action, and assuming that this commanded is immediately followed by open loop control where the pre-programmed basal delivery amount will be in effect thereafter; b) analyzing the future glucose level using this latest bolus value plus a future basal rate to determine if the future glucose level is acceptable, and if so, waiting for a selected period of time and repeating a); c) if the glucose level of b) is not acceptable, computing an alternate maximum temporary basal delivery amount that is lower than the previously assumed basal rate, such that the predicted future glucose level is acceptable, and if so, providing a temporary basal command at the computed basal rate and duration, and predicting a future glucose level; and if so, waiting for a selected period of time and repeating a); d) if the predicted future glucose level is unacceptable, projecting a future glucose level using the lowest temporary basal delivery rate computable in step c) and a maximum duration that is shorter than the maximum delivery duration, and, if the future glucose level is acceptable, providing a temporary basal command including the rate and duration of along with a nominal bolus command and then wait for a selected period of time and repeat a); and f) reducing the bolus command by minimum bolus resolution and repeat step a) such that the combination of the reduced bolus and a suitable temporary basal rate results in an acceptable predicted glucose profile if calculating a lower alternate temporary basal rate or a lower and shorter temporary basal rate does not result in an acceptable future glucose level. In still another aspect, the method further comprises alerting the user to take action to counter the effect of excessive insulin if an acceptable glucose profile cannot be obtained in step f) above.

In another aspect, the present invention includes a method for predicting insulin needs at a future time to avoid unwanted out of range alarms and adjusting current insulin delivery; comprising: providing a current glucose level; providing a future time when a predicted glucose level is required; determining the predicted level at the future time based upon the current glucose level, a value for insulin on board, current bolus parameters and current parameters defining an acceptable range of glucose levels; and adjusting insulin delivery to maintain the glucose level in a target range.

In yet another aspect, the present invention includes a method for reducing false hypoglycemic alarms in a system under closed loop control; comprising: a) providing a current glucose level; b) determining if the first level is below a threshold level and if so, providing a further glucose level at the expiration of a selected period of time; c) determining if the glucose level taken after the expiration of the selected period of time is below the threshold level, and if so, alerting the user of a low glucose condition if the time between providing the two glucose levels is greater than a selected duration of time, and if not, repeating c) until either the time since the current glucose level and the last further glucose level exceeds the selected duration of time or the last further glucose level is above the threshold level.

In yet another aspect, the present invention includes a method of adjusting glucose level alarm thresholds and alarm enunciation delay times in a system using CGM and insulin delivery system information, comprising using a model based state estimation, determining a predicted future glucose level and alerting a user only if the predicted future glucose level falls outside of a predetermined acceptable range. In an alternative aspect, the model based state estimation is a Kalman filter. In still another alternative aspect, the model based state estimation assesses the likelihood that a CGM measurement that exceeds a high or low threshold is due to a true event. In yet another alternative aspect, the model based state estimation assesses the likelihood that a CGM measurement that exceeds a high or low threshold is due to a sensor artifact.

In still another aspect, the likelihood is determined by comparing the difference between the latest CGM measurement and interstitial glucose computed by the model prior to the latest CGM measurement; and in a further aspect, the method comprises adjusting the glucose alarm enunciation by adjusting the threshold level and duration in which the CGM measurement exceeds a given threshold before an alarm is enunciated.

In yet another aspect, where a decreasing CGM signal close to a low threshold alarm value that is not accompanied by a corresponding amount of insulin history will result in a low threshold alarm being made less sensitive by lowering the threshold value and/or increasing the duration of delay before the CGM signal results in enunciation of a low threshold alarm. In an alternative aspect, where a decreasing CGM signal close to a low threshold alarm value that is accompanied by an insulin history that should have generated a much lower CGM value than is measured results in a low threshold alarm being made more sensitive by increasing the threshold value and/or decreasing the duration of delay before the CGM signal results in the enunciation of a low threshold alarm. In still another alternative aspect, where an increasing CGM signal close to a high threshold alarm value that is not accompanied by an appreciable amount of insulin history results in a high threshold alarm being made more sensitive by lowering the threshold value and/or decreasing the duration of delay before the CGM signal results in the enunciation of a high threshold alarm. In yet another alternative aspect, where an increasing CGM signal close to a high threshold alarm value that is accompanied by an appreciable amount of insulin history results in a high threshold alarm being made less sensitive by increasing the threshold value and/or increasing the duration of delay before the CGM signal results in the enunciation of a high threshold alarm.

In another aspect, the present invention a method of determining a latest insulin delivery amount and a temporary insulin delivery rate to be delivered when a closed loop insulin delivery system terminates unexpectedly, comprising a) providing a glucose level and predicting a future glucose level in order to determine the appropriate insulin amount for the latest control action, and assuming that this commanded is immediately followed by open loop control where the preprogrammed temporary basal rate will be in effect thereafter; b) analyzing the future glucose level using this latest insulin amount plus a future temporary basal rate to determine if the future glucose level is acceptable, and if so, waiting for a selected period of time and repeating a); c) if the glucose level of b) is not acceptable, computing an alternate maximum temporary basal delivery amount that is lower than the previously assumed basal rate, such that the predicted future glucose level is acceptable, and if so, providing a temporary basal command at the computed basal rate and duration, and predicting a future glucose level; and if so, waiting for a selected period of time and repeating a); d) if the predicted future glucose level is unacceptable, projecting a future glucose level using the lowest temporary basal delivery rate computable in c) and a maximum duration that is shorter than the maximum delivery duration, and, if the future glucose level is acceptable, providing a temporary basal command including the rate and duration of along with a nominal latest insulin delivery command and then wait for a selected period of time and repeat a); and f) reducing the latest insulin delivery command by a predetermined minimum insulin delivery resolution and repeat a) such that the combination of the reduced latest insulin delivery amount and a suitable temporary basal rate results in an acceptable predicted glucose profile if calculating a lower alternate temporary basal rate or a lower and shorter temporary basal rate does not result in an acceptable future glucose level.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

For the purposes of promoting an understanding of the principles of the invention, reference will now be made to a number of illustrative embodiments shown in the attached drawings and specific language will be used to describe the same. It will be understood that throughout this document, the terms "user" and "patient" are used interchangeably.

Figure 1:
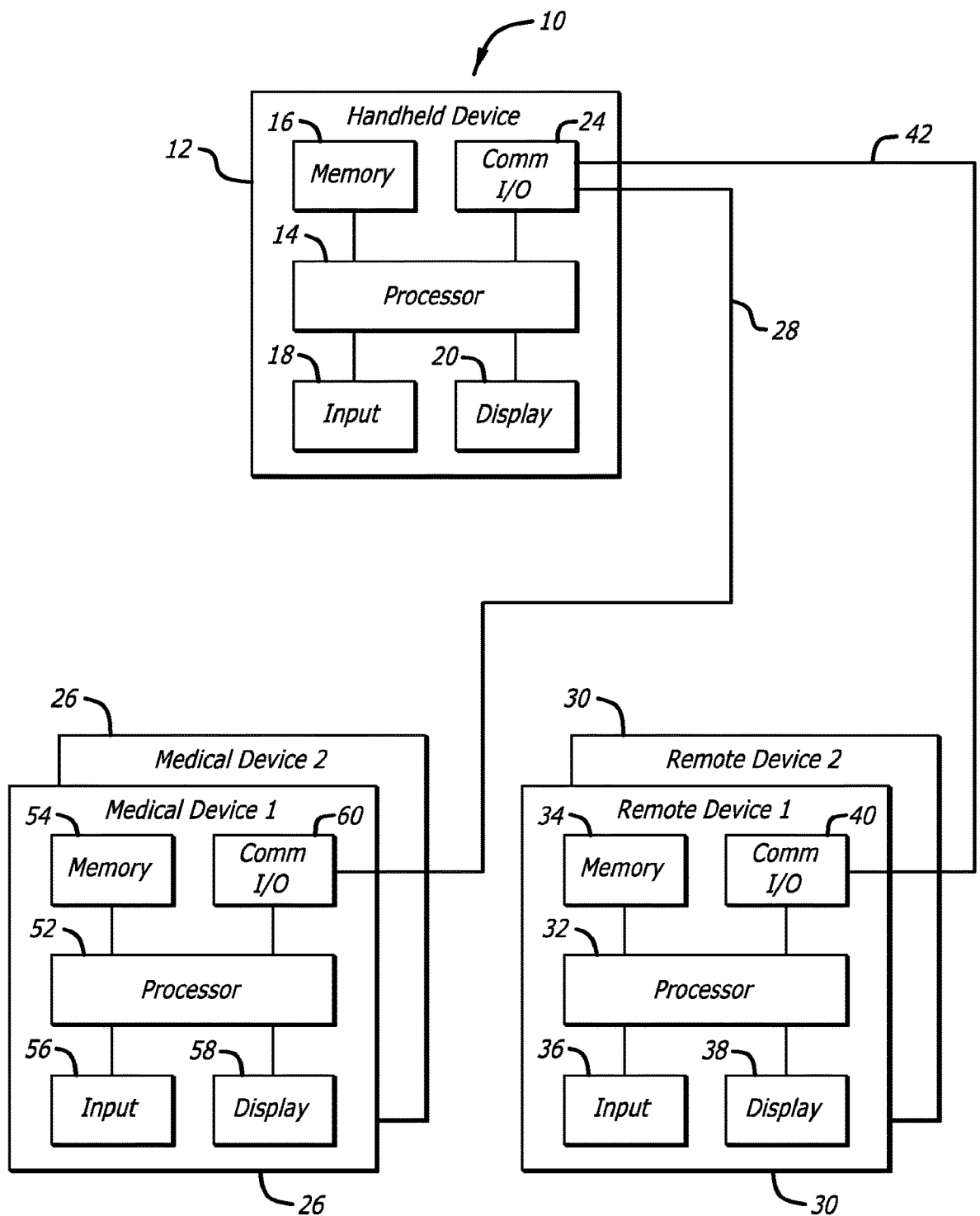
FIG. 1 is a schematic diagram illustrating an exemplary embodiment of a controller and its various components in operable communication with one or more medical devices, such as a glucose monitor or drug delivery pump, and optionally, in operable communication with a remote controller device.

Referring now to FIG. 1, a block diagram of one illustrative embodiment of a system 10 for determining drug administration information is shown. In the illustrated embodiment, the system 10 includes an electronic device 12, which may be handheld, having a processor 14 in data communication with a memory unit 16, an input device 18, a display 20, and a communication input/output unit 24. The electronic device 12 may be provided in the form of a general purpose computer, central server, personal computer (PC), lap top or notebook computer, personal data assistant (PDA), programmable telephone or cellular phone or other hand-held device, external infusion pump, glucose meter, analyte sensing system, or the like. The electronic device 12 may be configured to operate in accordance with one or more conventional operating systems including for example, but not limited to, the Windows® operating system (distributed by Microsoft Corporation), the Linux operating system, the Mac OS® (distributed by Apple, Inc.) and embedded operating systems such as the QNX® operating system (distributed by QNX Software Systems), the eCOS® operating system (distributed by eCosCentric Limited), Windows CE® (distributed by Microsoft Corporation) and the Palm® operating system (distributed by Palm Inc.), and may be configured to process data according to one or more conventional internet protocols for example, but not limited to, NetBios, TCP/IP and AppleTalk® (Apple, Inc.). In any case, the electronic device 12 forms part of a fully closed-loop, semi closed-loop, or open loop diabetes control system.

The processor 14 is microprocessor-based, although processor 14 may alternatively be formed of one or more general purpose and/or application specific circuits and operable as described hereinafter. The processor 14 is programmed using appropriate software commands that may be stored in the memory or communicated to the processor 14 as needed. The memory unit 16 includes sufficient capacity to store data, one or more software algorithms executable by the processor 14 and other data. The memory unit 16 may include one or more conventional memory or other data storage devices. Electronic device 12 may also include an integrated glucose meter for use in calibrating a continuous glucose monitor (CGM) or for calculating insulin amounts for bolus delivery.

The input device 18 may be used in a conventional manner to input and/or modify data. The display 20 is also included for viewing information relating to operation of the device 12 and/or system 10. Such a display may be a conventional display device including for example, but not limited to, a light emitting diode (LED) display, a liquid crystal display (LCD), a cathode ray tube (CRT) display, or the like. Alternatively or additionally, the display 20 may be or include an audible display configured to communicate information to a user, another person, or another electronic system having audio recognition capabilities via one or more coded patterns, vibrations, synthesized voice responses, or the like. Alternatively or additionally, the display 20 may be or include one or more tactile indicators configured to display or annunciate tactile information that may be discerned by the user or another person.

The input device 18 may be or include a conventional keyboard or keypad for entering alphanumeric data into the processor 14. Such a keyboard or keypad may include one or more keys or buttons configured with one or more tactile indicators to allow users with poor eyesight to find and select an appropriate one or more of the keys, and/or to allow users to find and select an appropriate one or more of the keys in poor lighting conditions. Alternatively or additionally, the input device 18 may be or include a conventional mouse or other conventional point and click device for selecting information presented on the display 20. Alternatively or additionally, the input device 18 may include the display 20 configured as a graphical user interface (GUI). In this embodiment, the display 20 may include one or more selectable inputs that a user may select by touching an appropriate portion of the display 20 using an appropriate implement. Alternatively, the display 20 may be configured as a touch-screen capable of responding to user activation to, for example, enter data or select device functions.

Alternatively, the input device 18 may also include a number of switches or buttons that may be activated by a user to select corresponding operational features of the device 12 and/or system 10. Input device 18 may also be or include voice-activated circuitry responsive to voice commands to provide corresponding input data to the processor 14. In any case, the input device 18 and/or display 20 may be included with or separate from the electronic device 12.

System 10 may also include a number of medical devices which carry out various functions, for example, but not limited to, monitoring, sensing, diagnostic, communication and treatment functions. In such embodiments, any of the one or more of the medical devices may be implanted within the user's body, coupled externally to the user's body (e.g., such as an infusion pump), or separate from the user's body. Alternatively or additionally, one or more of the medical devices may be mounted to and/or form part of the electronic device 12. Typically, the medical devices are each configured to communicate wirelessly with the communication I/O unit 24 of the electronic device 12 via one of a corresponding number of wireless communication links.

The wireless communications between the various components of the system 10 may be one-way or two-way. The form of wireless communication used may include, but is not limited to, radio frequency (RF) communication, infrared (IR) communication, Wi-Fi, RFID (inductive coupling) communication, acoustic communication, capacitive signaling (through a conductive body), galvanic signaling (through a conductive body), or the like. In any such case, the electronic device 12 and each of the medical devices include conventional circuitry for conducting such wireless communications circuit. Alternatively, one or more of the medical devices may be configured to communicate with the electronic device 12 via one or more conventional serial or parallel configured hardwire connections therebetween.

Each of the one or more medical devices 26 may include one or more of a conventional processing unit 52, conventional input/output circuitry and/or devices 56, 58 communication ports 60 and one or more suitable data and/or program storage devices 58. It will be understood that not all medical devices 26 will have the same componentry, but rather will only have the components necessary to carry out the designed function of the medical device. For example, in one embodiment, a medical device 26 may be capable of integration with electronic device 12 and remote device 30. In another embodiment, medical device may also be capable of standalone operation, should communication with electronic device 12 or remote device 30 be interrupted. In another embodiment, medical device 26 may include processor, memory and communication capability, but does not have a display 58 or input 56. In still another embodiment, the medical device 26 may include an input 56, but lack a display 58.

In some embodiments, the system 10 may alternatively or additionally include a remote device 30. The remote device 30 may include a processor 32, which may be identical or similar to the processor 14, a memory or other data storage unit 34, an input device 36, which may be or include any one or more of the input devices described hereinabove with respect to the input device 18, a display unit 38, which may be or include any one or more of the display units described hereinabove with respect to the display unit 20, and communication I/O circuitry 40. The remote device 30 may be configured to communicate with the electronic device 12 or medical devices(s) 26 via any wired or wireless communication interface 42, which may be or include any of the communication interfaces or links described hereinabove. Although not shown, remote device 30 may also be configured to communicate directly with one or more medical devices 26, instead of communicating with the medical device 26 through electronic device 12.

The system 10 illustrated in FIG. 1 is, or forms part of, a fully closed-loop, semi closed-loop, or open loop diabetes control arrangement. In this regard, the system 10 requires user input of some amount of information from which the system 10 determines, at least in part, insulin bolus administration information. Such insulin bolus administration information may be or include, for example, insulin bolus quantity or quantities, bolus type, insulin bolus delivery time, times or intervals (e.g., single delivery, multiple discrete deliveries, continuous delivery, etc.), and the like. Examples of user supplied information may be, for example but not limited to, user glucose concentration, interstitial glucose level information, information relating to a meal or snack that has been ingested, is being ingested, or is to be ingested sometime in the future, user exercise information, user stress information, user illness information, information relating to the user's menstrual cycle, and the like. In any case, the system 10 includes a delivery mechanism for delivering controlled amounts of a drug; such as, for example, insulin, glucagon, incretin, or the like, and/or offering an alternatively actionable therapy recommendation to the user via the display 20, such as, for example, directions or instructions related to ingesting carbohydrates, exercising, and the like.

The system 10 may be provided in any of a variety of configurations, and examples of some such configurations will now be described. It will be understood, however, that the following examples are provided merely for illustrative purposes, and should not be considered limiting in any way. Those skilled in the art may recognize other possible implementations of a fully closed-loop, semi closed-loop, or open loop diabetes control arrangement, and any such other implementations are contemplated by this disclosure.

In a first exemplary implementation of the system 10, the electronic device 12 is provided in the form of an insulin pump configured to be worn externally to the user's body and also configured to controllably deliver insulin to the user's body. In this example, the medical devices 26 may include one or more implanted sensors and/or sensor techniques for providing information relating to the physiological condition of the user. Examples of such implanted sensors may include, but should not be limited to, a glucose sensor, a body temperature sensor, a blood pressure sensor, a heart rate sensor, one or more bio-markers configured to capture one or more physiological states of the body, such as, for example, HBA1C, or the like.

In implementations that include an implanted glucose sensor, the system 10 may be a fully closed-loop system operable in a conventional manner to automatically monitor glucose and deliver insulin, as appropriate, to maintain glucose at desired levels. The various medical devices may alternatively or additionally include one or more sensors or sensing systems that are external to the user's body and/or sensor techniques for providing information relating to the physiological condition of the user. Examples of such sensors or sensing systems may include, but should not be limited to, a glucose strip sensor/meter, a body temperature sensor, a blood pressure sensor, a heart rate sensor, one or more bio-markers configured to capture one or more physiological states of the body, such as, for example, HBA1C, or the like.

In implementations that include an external glucose sensor, the system 10 may be a closed-loop, semi closed-loop, or open loop system operable in a conventional manner to deliver insulin, as appropriate, based on glucose information provided thereto by the user. Information provided by any such sensors and/or sensor techniques may be communicated to the system 10 using any one or more conventional wired or wireless communication techniques. In this exemplary implementation, the remote device 30 may also be included in the form of a handheld or otherwise portable electronic device configured to communicate information to and/or from the electronic device 12.

In a second exemplary implementation of the system 10, the electronic device 12 is provided in the form of a handheld remote device, such as a PDA, programmable cellular phone, or other handheld device. In this example, the medical devices 26 include at least one conventional implantable or externally worn drug pump. In one embodiment of this example, an insulin pump is configured to controllably deliver insulin to the user's body. In this embodiment, the insulin pump is configured to wirelessly transmit information relating to insulin delivery to the handheld device 12. The handheld device 12 is configured to monitor insulin delivery by the pump, and may further be configured to determine and recommend insulin bolus amounts, carbohydrate intake, exercise, and the like. The system 10 may or may not be configured in this embodiment to provide for transmission of wireless information from the handheld device 12 to the insulin pump.

In an alternate embodiment of this example, the handheld device 12 is configured to control insulin delivery to the user by determining insulin delivery commands and transmitting such commands to the insulin pump. The insulin pump, in turn, is configured to receive the insulin delivery commands from the handheld device 12, and to deliver insulin to the user according to the commands. The insulin pump, in this embodiment, may or may not further process the insulin pump commands provided by the handheld unit 12. In any case, the system 10 will typically be configured in this embodiment to provide for transmission of wireless information from the insulin pump back to the handheld device 12 to thereby allow for monitoring of pump operation. In either embodiment of this example, the system 10 may further include one or more implanted and/or external sensors of the type described in the previous example. In this exemplary implementation, a remote device 30 may also be included in the form of, for example, a PC, PDA, programmable cellular phone, laptop or notebook computer configured to communicate information to and/or from the electronic device 12.

Those skilled in the art will recognize other possible implementations of a fully closed-loop, semi closed-loop, or open loop diabetes control arrangement using at least some of the components of the system 10 illustrated in FIG. 1. For example, the electronic device 12 in one or more of the above examples may be provided in the form of a PDA, programmable cellular phone, laptop, notebook or personal computer configured to communicate with one or more of the medical devices 26, at least one of which is an insulin delivery system, to monitor and/or control the delivery of insulin to the user. As another example, the remote device 30 may be configured to communicate with the electronic device 12 and/or one or more of the medical devices 26, to control and/or monitor insulin delivery to the patient, and/or to transfer one or more software programs and/or data to the electronic device 12. The remote device 30 may reside in a caregiver's office or other remote location, and communication between the remote device and any component of the system 10 may be accomplished via an intranet, internet (such as, for example, through the world-wide-web), cellular, telephone modem, RF, or other communication link. Any one or more conventional internet protocols may be used in such communications. Alternatively or additionally, any conventional mobile content delivery system; such as, for example, Wi-Fi, WiMAX, short message system (SMS), or other conventional message scheme may be used to provide for communication between devices comprising the system 10.

Generally, the concentration of glucose in a person changes as a result of one or more external influences such as meals and exercise, and also changes resulting from various physiological mechanisms such as stress, illness, menstrual cycle and the like. In a person with diabetes, such changes can necessitate monitoring the person's glucose level and administering insulin or other glucose level altering drug, such as, for example, a glucose lowering or raising drug, as needed to maintain the person's glucose level within a desired range. In any of the above examples, the system 10 is thus configured to determine, based on some amount of patient-specific information, an appropriate amount, type and/or timing of insulin or other glucose level altering drug to administer in order to maintain normal glucose levels without causing hypoglycemia or hyperglycemia. In some embodiments, the system 10 is configured to control one or more external insulin pumps, such as, for example, subcutaneous, transcutaneous or transdermal pumps, and/or implanted insulin pumps to automatically infuse or otherwise supply the appropriate amount and type of insulin to the user's body in the form of one or more insulin boluses.

In other embodiments, the system 10 is configured to display or otherwise notify the user of the appropriate amount, type, and/or timing of insulin in the form of an insulin delivery or administration recommendation or instruction. In such embodiments, the hardware and/or software forming system 10 allows the user to accept the recommended insulin amount, type, and/or timing, or to reject it. If the recommendation is accepted by the user, the system 10, in one embodiment, automatically infuses or otherwise provides the appropriate amount and type of insulin to the user's body in the form of one or more insulin boluses. If, on the other hand, the user rejects the insulin recommendation, the hardware and/or software forming system 10 allows the user to override the system 10 and manually enter values for insulin bolus quantity, type, and/or timing in the system. The system 10 is thus configured by the user to automatically infuse or otherwise provide the user specified amount, type, and/or timing of insulin to the user's body in the form of one or more insulin boluses.

Alternatively, the appropriate amount and type of insulin corresponding to the insulin recommendation displayed by the system 10 may be manually injected into, or otherwise administered to, the user's body. It will be understood, however, that the system 10 may alternatively or additionally be configured in like manner to determine, recommend, and/or deliver other types of medication to a patient.

The system 10 is operable, as just described, to determine and either recommend or administer an appropriate amount of insulin or other glucose level lowering drug to the patient in the form of one or more insulin boluses. In order to determine appropriate amounts of insulin to be delivered or administered to the user to bring the user's glucose level within an acceptable range, the system 10 requires at least some information relating to one or more external influences and/or various physiological mechanisms associated with the user. For example, if the user is about to ingest, is ingesting, or has recently ingested, a meal or snack, the system 10 generally requires some information relating to the meal or snack to determine an appropriate amount, type and/or timing of one or more meal compensation boluses of insulin. When a person ingests food in the form of a meal or snack, the person's body reacts by absorbing glucose from the meal or snack over time. For purposes of this document, any ingesting of food may be referred to hereinafter as a "meal," and the term "meal" therefore encompasses traditional meals, such as, for example, breakfast, lunch and dinner, as well as intermediate snacks, drinks, and the like.

Figure 2:
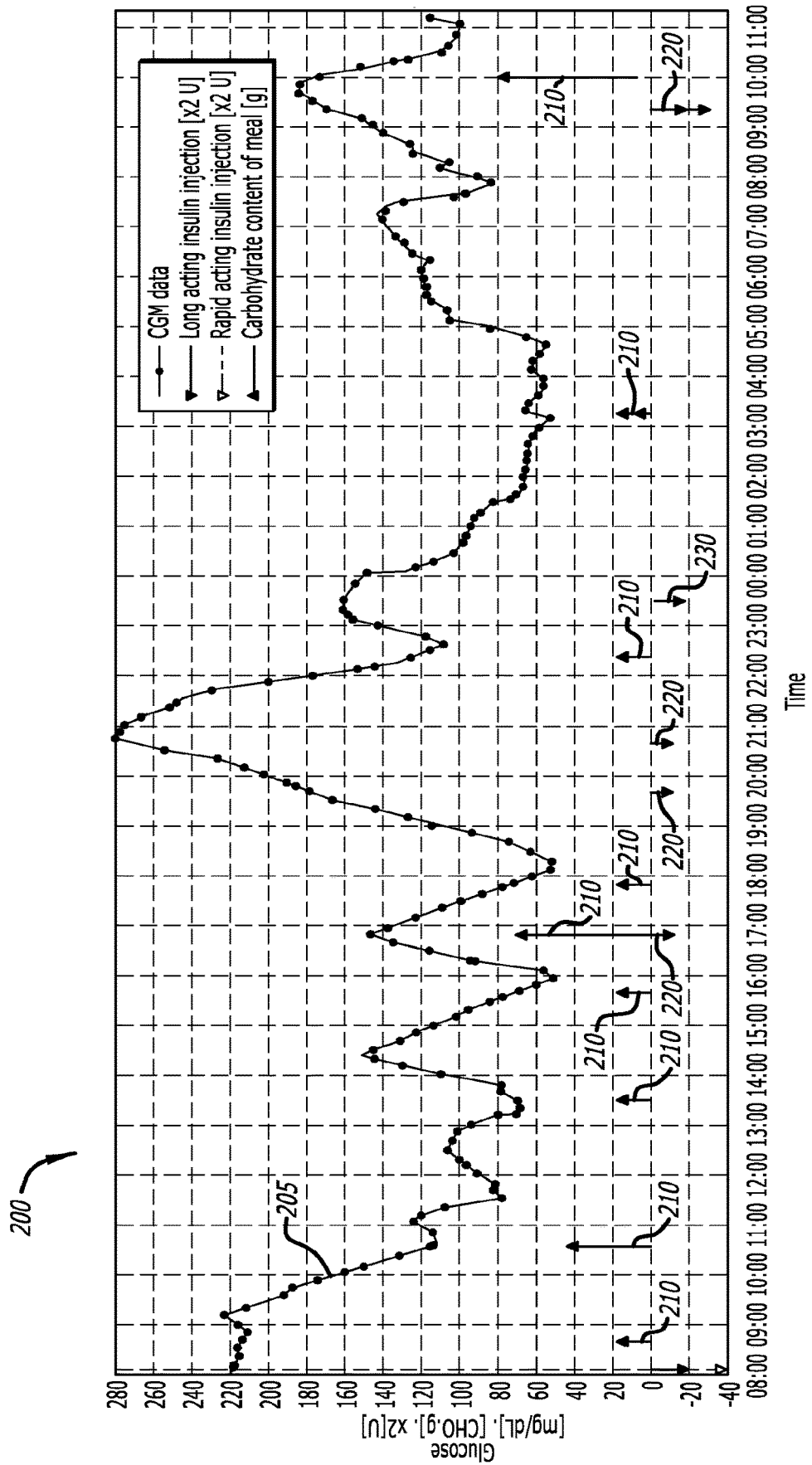
FIG. 2 is a graphical representation of a glucose profile showing glucose level measured using a CGM sensor as a function of time, and also showing the variation of the glucose level as function of carbohydrate intake and insulin administration.

FIG. 2 depicts a typical glucose absorption profile 200 for a user measured using a CGM sensor. The graph 205 plots the measured glucose level as a function of time. This profile shows the effect on glucose level of various actions, such as carbohydrate intake 210, and the delivery of rapid acting insulin 210 and long acting insulin 230.

The general shape of a glucose absorption profile for any person rises following ingestion of the meal, peaks at some measurable time following the meal, and then decreases thereafter. The speed, that is, the rate from beginning to completion, of any one glucose absorption profile typically varies for a person by meal composition, meal type or time (such as, for example, breakfast, lunch, dinner, or snack) and/or according to one or more other factors, and may also vary from day-to-day under otherwise identical meal circumstances. Generally, the information relating to such meal intake information supplied by the user to the system 10 should contain, either explicitly or implicitly, an estimate of the carbohydrate content of the meal or snack, corresponding to the amount of carbohydrates that the user is about to ingest, is ingesting, or has recently ingested, as well as an estimate of the speed of overall glucose absorption from the meal by the user.

The estimate of the amount of carbohydrates that the patient is about to ingest, is ingesting, or has recently ingested, may be provided by the user in any of various forms. Examples include, but are not limited to, a direct estimate of carbohydrate weight (such as, for example, in units of grams or other convenient weight measure), an amount of carbohydrates relative to a reference amount (such as, for example, dimensionless), an estimate of meal or snack size (such as, for example, dimensionless), and an estimate of meal or snack size relative to a reference meal or snack size (such as, for example, dimensionless). Other forms of providing for user input of carbohydrate content of a meal or snack will occur to those skilled in the art, and any such other forms are contemplated by this disclosure.

The estimate of the speed of overall glucose absorption from the meal by the user may likewise be provided by the user in any of various forms. For example, for a specified value of the expected speed of overall glucose absorption, the glucose absorption profile captures the speed of absorption of the meal taken by the user. As another example, the speed of overall glucose absorption from the meal by the user also includes time duration between ingesting of the meal by a user and the peak glucose absorption of the meal by that user, which captures the duration of the meal taken by the user. The speed of overall glucose absorption may thus be expressed in the form of meal speed or duration. Examples of the expected speed of overall glucose absorption parameter in this case may include, but are not limited to, a compound parameter corresponding to an estimate of the meal speed or duration (such as, for example, units of time), a compound parameter corresponding to meal speed or duration relative to a reference meal speed or duration (such as, for example, dimensionless), or the like.

As another example of providing the estimate of the expected speed of overall glucose absorption parameter, the shape and duration of the glucose absorption profile may be mapped to the composition of the meal. Examples of the expected speed of overall glucose absorption parameter in this case may include, but are not limited to, an estimate of fat amount, protein amount and carbohydrate amount (such as, for example, in units of grams) in conjunction with a carbohydrate content estimate in the form of meal size or relative meal size, an estimate of fat amount, protein amount and carbohydrate amount relative to reference fat, protein and carbohydrate amounts in conjunction with a carbohydrate content estimate in the form of meal size or relative meal size, and an estimate of a total glycemic index of the meal or snack (such as, for example, dimensionless), wherein the term "total glycemic index" is defined for purposes of this document as a parameter that ranks meals and snacks by the speed at which the meals or snacks cause the user's glucose level to rise. Thus, for example, a meal or snack having a low glycemic index produces a gradual rise in glucose level whereas a meal or snack having a high glycemic index produces a fast rise in glucose level. One exemplary measure of total glycemic index may be, but is not limited to, the ratio of carbohydrates absorbed from the meal and a reference value, such as, for example, derived from pure sugar or white bread, over a specified time period, such as, for example, 2 hours. Other forms of providing for user input of the expected overall speed of glucose absorption from the meal by the patient, and/or for providing for user input of the expected shape and duration of the glucose absorption profile generally will occur to those skilled in the art, and any such other forms are contemplated by this disclosure. [0054] Generally, the concentration of glucose in a person with diabetes changes as a result of one or more external influences such as meals and/or exercise, and may also change resulting from various physiological mechanisms such as stress, menstrual cycle and/or illness. In any of the above examples, the system 10 responds to the measured glucose by determining the appropriate amount of insulin to administer in order to maintain normal glucose levels without causing hypoglycemia. In some embodiments, the system 10 is implemented as a discrete system with an appropriate sampling rate, which may be periodic, aperiodic or triggered, although other continuous systems or hybrid systems may alternatively be implemented as described above.

As one example of a conventional diabetes control system, one or more software algorithms may include a collection of rule sets which use (1) glucose information, (2) insulin delivery information, and/or (3) user inputs such as meal intake, exercise, stress, illness and/or other physiological properties to provide therapy, and the like, to manage the user's glucose level. The rule sets are generally based on observations and clinical practices as well as mathematical models derived through or based on analysis of physiological mechanisms obtained from clinical studies. In the exemplary system, models of insulin pharmacokinetics and pharmacodynamics, glucose pharmacodynamics, meal absorption and exercise responses of individual patients are used to determine the timing and the amount of insulin to be delivered. A learning module may be provided to allow adjustment of the model parameters when the patient's overall performance metric degrades such as, for example, adaptive algorithms, using Bayesian estimates, may be implemented. An analysis model may also be incorporated which oversees the learning to accept or reject learning. Adjustments are achieved utilizing heuristics, rules, formulae, minimization of cost function(s) or tables (such as, for example, gain scheduling).

Predictive models can be programmed into the processor(s) of the system using appropriate embedded or inputted software to predict the outcome of adding a controlled amount of insulin or other drug to a user in terms of the an expected glucose value. The structures and parameters of the models define the anticipated behavior.

Any of a variety of conventional controller design methodologies, such as PID systems, full state feedback systems with state estimators, output feedback systems, LQG (Linear-Quadratic-Gaussian) controllers, LQR (Linear-Quadratic-Regulator) controllers, eigenvalue/eigenstructure controller systems, and the like, could be used to design algorithms to perform physiological control. They typically function by using information derived from physiological measurements and/or user inputs to determine the appropriate control action to use. While the simpler forms of such controllers use fixed parameters (and therefore rules) for computing the magnitude of control action, the parameters in more sophisticated forms of such controllers may use one or more dynamic parameters. The one or more dynamic parameters could, for example, take the form of one or more continuously or discretely adjustable gain values. Specific rules for adjusting such gains could, for example, be defined either on an individual basis or on the basis of a user population, and in either case will typically be derived according to one or more mathematical models. Such gains are typically scheduled according to one or more rule sets designed to cover the expected operating ranges in which operation is typically nonlinear and variable, thereby reducing sources of error.

Model based control systems, such as those utilizing model predictive control algorithms, can be constructed as a black box wherein equations and parameters have no strict analogs in physiology. Rather, such models may instead be representations that are adequate for the purpose of physiological control. The parameters are typically determined from measurements of physiological parameters such as glucose level, insulin concentration, and the like, and from physiological inputs such as food intake, alcohol intake, insulin doses, and the like, and also from physiological states such as stress level, exercise intensity and duration, menstrual cycle phase, and the like. These models are used to estimate current glucose level or to predict future glucose levels. Such models may also take into account unused insulin remaining in the user after a bolus of insulin is given, for example, in anticipation of a meal. Such unused insulin will be variously described as unused, remaining, or "insulin on board."

Insulin therapy is derived by the system based on the model's ability to predict glucose levels for various inputs. Other conventional modeling techniques may be additionally or alternatively used to predict glucose levels, including for example, but not limited to, building models from first principles.

In a system as described above, the controller is typically programmed to provide a "basal rate" of insulin delivery or administration. Such a basal rate is the rate of continuous supply of insulin by an insulin delivery device such as a pump that is used to maintain a desired glucose level in the user. Periodically, due to various events that affect the metabolism of a user, such as eating a meal or engaging in exercise, a "bolus" delivery of insulin is required. A "bolus" is defined as a specific amount of insulin that is required to raise the blood concentration of insulin to an effective level to counteract the affects of the ingestion of carbohydrates during a meal and also takes into account the affects of exercise on the glucose level of the user.

As described above, an analyte monitor may be used to continuously monitor the glucose level of a user. The controller is programmed with appropriate software and uses models as described above to predict the effect of carbohydrate ingestion and exercise, among other factors, on the predicted level of glucose of the user at a selected time. Such a model must also take into account the amount of insulin remaining in the blood stream from a previous bolus or basal rate infusion of insulin when determining whether or not to provide a bolus of insulin to the user.

In a typical situation, an insulin pump normally delivers insulin without user intervention when delivering the insulin at the basal insulin delivery rate. At times, however, the pump may detect conditions that warrant providing an alarm or other signal to the user that intervention in the insulin delivery by the user is necessary. Depending on the conditions and the user's response, the controller may instruct the pump to stop delivering insulin.

When insulin delivery is stopped, the user will eventually need to restart insulin delivery. In view of the period of time during which insulin delivery was stopped, the user may need to deliver a correction bolus of insulin to bring their glucose level back within an acceptable range. The volume of the insulin bolus is calculated by the user from their current glucose level and their experience with managing their diabetes. For example, users who have experience in managing their diabetes are typically able to estimate the various factors that need to be considered in calculating a corrective bolus dosage of insulin.

In one example, the size of the corrective bolus required to maintain the user in euglycemia is related to the manner and duration in which delivery of insulin was stopped. For example, if insulin delivery was stopped for a few minutes, perhaps no corrective bolus of insulin is required. However, if insulin delivery is stopped for several hours, a significant bolus of insulin may be required to bring the user's glucose level into an acceptable range.

The controller of the system monitors the insulin pump and when the pump determines that the user wants to restart the pump, the pump may either confirm that the user wants to restart basal rate delivery of insulin, or it may prompt the user to administer a manual bolus of insulin.

In one embodiment of the invention, the controller and/or pump has a memory that stores information related to the history of the user's glucose levels and various actions or events that have been taken to adjust those levels, such as the rate of basal delivery of insulin, the amount of the last insulin bolus delivery, and the time between various events or user actions. The controller and/or pump may also store the time that has elapsed since the pump was stopped. Additional factors that may be considered include the user's insulin sensitivity, the amount of insulin that may remain in the user's blood stream since the last basal or bolus insulin delivery and whether or not an event or action may have incurred that would cause the basal rate of insulin delivery to have changed since the pump was stopped.

When the user desires to restart the pump, the controller and/or pump may, using the data programmed within the memory regarding the user's history of insulin delivery and glucose levels resulting therefrom, calculate a bolus volume of insulin to deliver using a model such as set forth as:

Remaining insulin=delivered volume×(IATIME−time)/IATIME,

Where:
Delivered volume is the amount of insulin delivered,
time is the time since the insulin was delivered, and
IATIME is the user's insulin action time, which is a measure of how long insulin remains
active in an individual user's body.

Those skilled in the art will understand that other models can be used to perform this estimation, such as, for example, the decaying exponential model or model using an S-model decay.

For basal delivery, the times since the insulin was last delivered, or the age of the delivery, is not a constant. The calculation is a convolution of the basal profile function and the linear decay function.

In practice, basal insulin delivery is not delivered continuously, but instead is accumulated and delivered at discrete times. For example, an exemplary insulin pump may be programmed to deliver three minutes of basal rate insulin delivery spaced three minutes apart. This simplifies the above calculation to the dot product of two vectors. For example, D=vector of deliveries that were not performed, oldest to newest. For example, D=(0.3, 0.3, 0.3, 0.3, 0.3, 0.3, 0.3, 0.3, 0.3, 0.3, 0.5, 0.5, 0.5, 0.5, 0.5, 0.5, 0.5, 0.5, 0.5, 0.5) which represents 20 deliveries of 0.3 and 0.5 units spaced three minutes apart. Similarly, T=vector or time multipliers.

For example, if the insulin action time of the patient is 60 minutes and delivery has been stopped for 42 minutes, then:

T equals (0.00, 0.00, 0.00, 0.00, 0.00, 0.00, 0.35, 0.40, 0.45, 0.50, 0.55, 0.60, 0.65, 0.70, 0.75, 0.80, 0.85, 0.90, 0.95, 1.00).

The dot product of D*T equal 4.39 units.

Thus, for this example, the user will need to either manually administer or program the pump to administer 4.39 units of insulin, the bolus volume that will provide the same value for the insulin onboard for the user had the basal delivery of insulin not been stopped.

In another embodiment of the present invention using a closed looped control system, the controller or pump may be programmed to perform a model-based calculation of transitory insulin using an insulin bolus command as the nominal input for the model. This process provides a means to use model-based calculation of insulin onboard (JOB) past insulin delivery information, and past and present glucose information and predicted glucose profile over a near-future horizon to determine a safe amount and duration of basal rate in the event that a closed loop system that normally uses bolus insulin deliver terminates its operation unexpectedly.

Automated closed loop systems that regulate glucose levels by using insulin delivery have to account for instances when the closed loop system terminates and switches to open loop control. For users with insulin pumps, open-loop operation typically includes a pre-programmed insulin basal rate as well as a bolus insulin delivery rate administered in response to known events, such as a meal. When a system transitions from open to closed loop, past insulin delivery information is available from the memory and can be used by the closed loop controller to determine the best and safest insulin delivery profile for the user.

One hazard mitigated by this process is related to the transition from closed loop to open loop operation, such as, for example, in the case where a controller under closed loop control has determined a series of insulin commands that may require subsequent insulin deliveries to be lower than the open loop pre-programmed basal insulin delivery rate. As long as the system remains in closed loop operation, this is not an issue. However, should the system transition to open loop operation, having the pump deliver insulin at the pre-programmed basal rate could result in unwanted hypoglycemia if the controller previously ordered the pump to deliver insulin at a rate and duration that resulted in a large residual IOB with a plan to control the delivery in the future to significantly reduce the insulin delivery at a rate below the pre-programmed basal rate.

One embodiment of the invention addresses the situation where the closed loop system operates by delivering bolus insulin commands at a fixed interval in time, and the closed-loop system periodically obtains glucose measurement from a glucose measuring device. Such a system is also capable of issuing a temporary basal rate command to the pump with a specified amount and duration in which the basal command should apply since the command was issued. When the duration of such a demand expires, the system reverts to the pre-programmed basal rate.

As used in this description of the various embodiments of the invention, the latest command intended for normal operation of the system is described in terms of "bolus commands." Alternatively, the safety command intended to be used when closed loop operation of the system is interrupted is described in terms of a "temporary basal rate" command. The replacement of the normal operation command in terms of bolus with basal rate does not change the mechanism of the various embodiments of the invention. Using bolus and basal rate for the normal operation and the safety-related commands clarifies the roles of those commands in the description of the various embodiments of the invention included herein.

In another embodiment of the invention, the closed loop system is able to track the IOB amount by utilizing insulin pharmacokinetic and pharmacodynamic models, and by keeping track of insulin delivery data corresponding to the actual delivery of insulin to the user. This delivery data includes bolus and basal insulin amounts commanded by the user or by the automated closed loop controller.

For example, the model used by the controller to calculate insulin delivery rates may utilize a pharmacokinetic model, such as a modified version of a model used by Hovorka et al.:

$$\frac{\partial(i1(t))}{\partial t} = \frac{-1(t)}{tau\_i} + u(t)$$

$$\frac{\partial(i2(t))}{\partial(t)} = -\frac{[i2(t) - i1(t)]}{tau\_i}$$

$$i(t) = \frac{i2(t)}{MCRWtau\_i}$$

Where:
(t) denotes variables and/or states that vary in time;
u(t) is the amount of insulin bolus given at any time t;
i1(t) and i2(t) are internal states of the insulin absorption;
i(t) is the plasma insulin concentration;
tau i is the time-to-peak of insulin absorption;
MCR is the metabolic clearance rate; and
W is the user's weight.

An example of an insulin pharmacodynamic model that may be programmed into the controller or pump using suitable software or hardware commands is given by:

$$\frac{\partial(x(t))}{\partial t} = -p1[x(\ )t) - i(t)]$$

$$\frac{\partial(g(t))}{dt} = -[Sg + [Si \cdot x(t)]]g(t) = [Sg \cdot g)(t)] + Sm \cdot \frac{\partial(gm(t))}{dt}$$

Where:
Sg is the glucose clearance rated independent of insulin;
Si is the glucose clearance rate due to insulin;
g0(t) is a slowly varying equilibrium for the glucose clearance independent of insulin;
Sm is the glucose appearance constant due to meal absorption; and $$\frac{\partial(gm(t)}{\partial t}$$

is the rate of glucose appearance due to meal absorption.

In this model, the first equation governs the effective insulin x(t) over time as a function of plasma insulin i(t), given a decay time constant of 1/pl. The second equation governs how glucose g(t) varies over time as a function of many factors, including, for example, the insulin pharmacodynamics −Si x(t) g(t).

At any given time, the closed loop system is able to estimate the latest glucose by utilizing the IOB data, insulin history, glucose measurements, and a physiological model of glucose in response to insulin and other measurable factors, such as exercise and meal estimate and/or announcements. Additionally, at any time, the closed loop system in one embodiment of the invention is able to compute a desired bolus command that would result in the present and projected glucose of the user in a selected near future horizon falling within a specified nominal target, or one that optimizes the present and projected glucose with respect to some robust optimality criteria. This is a typical process involved in automatic closed looped systems that are model-based, such as a model-based approach that falls under the model predictive control (MPC) architecture.

When the system receives a temporary basal command, the closed loop system may, given the JOB, insulin history, glucose history, predicted glucose (in the near future horizon), and pre-programmed basal insulin delivery rate, compute a temporary basal amount and duration such that if the closed loop operation of the system terminates, the combination of the basal rate of that amount and the specified duration and the subsequent transition to the pre-programmed basal rate is such that the predicted glucose value of the user in the foreseeable future horizon will remain within a specified safe target. This safe target may be different from the specified nominal target value for the optimal calculation, in that it can be designed to be more conservative from a hazards prevention perspective.

Figure 3:
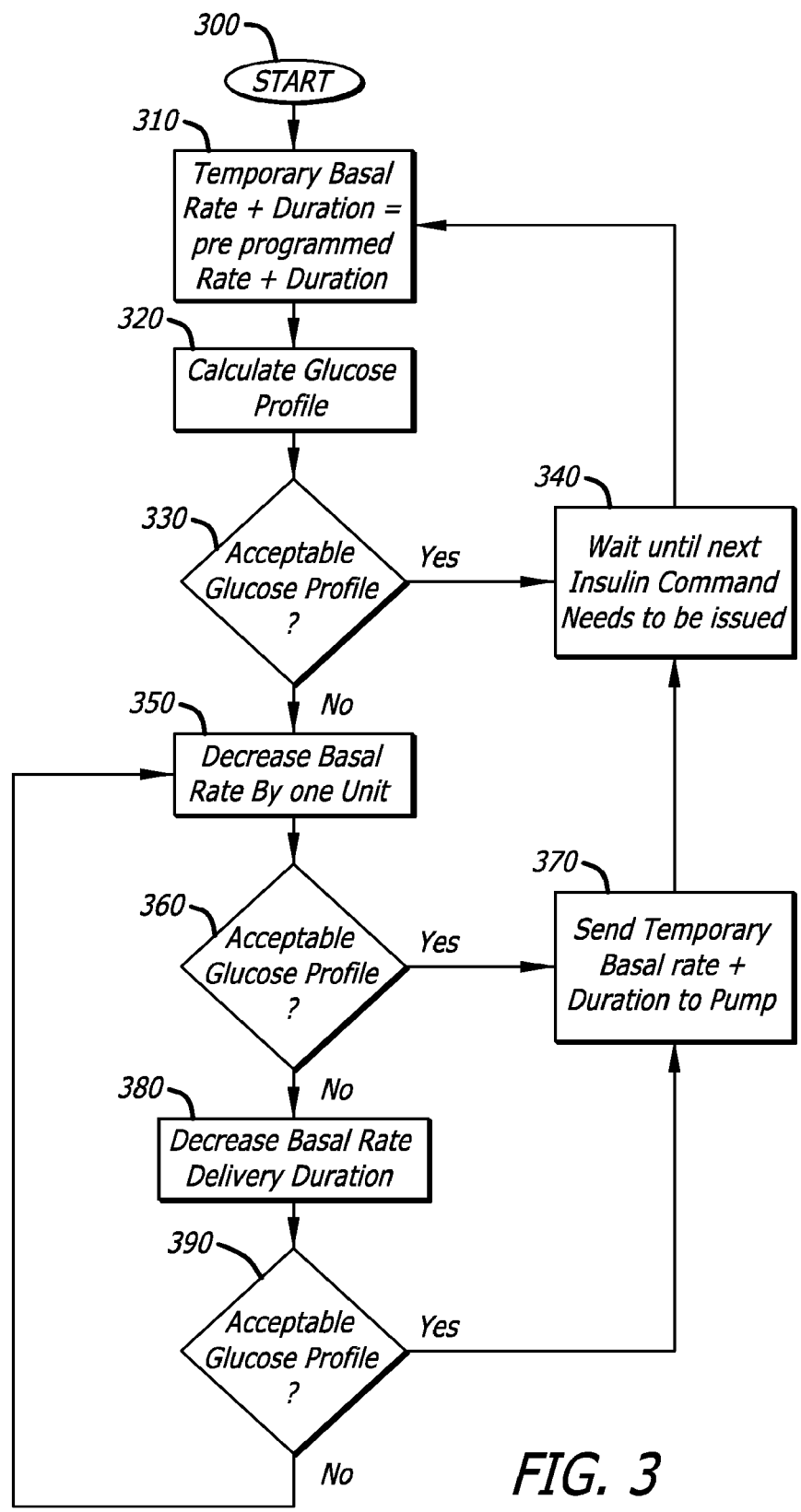
FIG. 3 is a block diagram illustrating an embodiment of the present invention.

An example of a process for determining a temporary basal rate of insulin delivery, along with the duration of that basal rate delivery, is illustrated by the diagram of FIG. 3. Appropriate software or hardware commands may be used to program the processor of the pump and/or controller to carry out the illustrated steps. Using a heuristic process, a glucose value may be predicted into the near future horizon under an assumption that the commanded bolus insulin delivery at present is followed by an immediate transfer to the programmed basal rate. In other words, the temporary basal rate candidate value calculated using the heuristic by the controller is identical to the pre-programmed basal rate.

Using this information as a starting point in box 310 as input into the selected model, a predicted glucose profile for a future time is calculated in box 320. If an acceptable predicted glucose profile results from this calculation in box 330, when there is no need to issue a temporary basal rate of any duration to maintain the user's glucose level within an acceptable range. When this is the case, the system waits until the next time an insulin command needs to be issued in box 340. When the next insulin command is determined to be needed, the processor begins at box 310, and once again carries out the process wherein glucose is predicted into the near future horizon as stated above.

If an acceptable predicted glucose profile does not result from the calculation carried out by the processor of the controller, the temporary basal insulin delivery rate is decreased by one value lower from the previous temporary basal rate candidate in box 350. The resolution of the basal rate for the particular pump and/or controller and/or glucose sensor determines the size of the reduction of basal rate that will be applied. This calculation may assume the maximum delivery duration allowable by the system.

If this assumption results in an acceptable predicted glucose profile in box 360, then a temporary basal insulin delivery command is sent using this basal rate and duration along with the nominal bolus command to the pump in box 370. The controller then waits until the next time an insulin command needs to be issued, and then restarts the process at box 310 again.

If an acceptable glucose profile is not calculated in box 360, the process keeps the same temporary basal rate as was used in box 350, and the decreases the duration of the basal rate delivery by an amount that is a function of system's resolution on command duration in box 380. If this calculation results in an acceptable predicted glucose profile in box 290, then a temporary basal command using this basal rate and duration along with the nominal bolus command is sent to the pump in box 370. Again, the controller waits until the next time an insulin command needs to be issued in box 340. When that time occurs, the process begins again box 310.

The iterative process described above is continued until the lowest allowable basal rate of insulin delivery is reached. If this assumption does not result in an acceptable predicted glucose profile, then the bolus command is reduced such that the combination of the reduced bolus rate and the temporary basal rate results in an acceptable predicted glucose profile.

If this is not possible, then an alert is sent to the user to take rescue carbohydrates or other actions that counteract the effect of excessive insulin.

The purpose of the above-described process is to add an additional safety calculation layer for the process control provided by automated closed-loop algorithms such that the closed-loop system computes two scenarios. First, the common scenario where insulin commands are issued and acted upon without interruption in the foreseeable future. This is normally computed by the automated closed-loop systems using model based approaches such as MPC. Second, the hazard-mitigated scenario where the sequence of insulin commands are abruptly interrupted after the latest command. The process set forth above addresses this scenario.

Using such a system, the embodiments of the present invention use model-based principles and available data to predict more than one scenario of insulin delivery such that when the periodic normal insulin command is interrupted, the system does not cause an unwanted hypoglycemic hazard. Avoiding unwanted hypoglycemia is important in providing proper control of glucose level in the diabetic user. The various embodiments of the invention provide better hazard mitigation against the risk of hypoglycemia due to a combination of insulin stacking (where a user already has an amount of insulin on board, but administers an additional bolus of insulin, often driving the user's glucose level towards hypoglycemia) and termination of closed-loop control. Utilizing a model-based approach improves the hazard mitigation caused by interruption of the automated closed-loop system, even though the interruption may have been accompanied by an alert/alarm or a temporary basal rate with a fixed duration.

In a CGM device such as the FreeStyle Navigator® Continuous Glucose Monitoring System that is distributed by Abbott Diabetes Care, there is a mute alarm feature that allows the user to mute the alarm when it is not easy for the user to respond to the alarm. Such alarms occur, for example, when the user's glucose level is either in the hyperglycemic range or, more importantly, in the hypoglycemic range.

For example, the user may choose to mute the alarm for the next two hours knowing that the user will be in a long meeting and does not want the alarm to disturb anyone. However, in the case of a low alarm signifying hypoglycemia, muting the alarm may lead to failure of the user to treat the hypoglycemic condition, which could be dangerous. The situation would be improved if at the time the user is muting the alarm, the system checks to determine the likelihood that the user may become hypoglycemic within the period of time that the alarm is muted. Generally, the system calculates a projected low-glucose level using IOB and real-time information to fine tune the projection and providing an alarm to indicate low glucose values. The problem with a persistent projected alarm, however, is the additional user annoyance associated with false positives. A user-initiated approach allows the user to define the time period that he wishes to have more precaution built into the control system as opposed to the system simply providing a persistent alarm to the user indicating that the controller has determined that some correction action is necessary, but at a time that a user is either unable or unwilling to take such action.

In one embodiment, the invention uses an overall strategy of potential low alarm detection to preempt pump control modification. Such a determination is useful during activities or events such as where the user goes to a long meeting or attends an event such as a movie, theatre, concert, or a long drive that may create a barrier from detecting and acting on a low-glucose level alarm. Another situation where the various embodiments of the invention are advantageous is where the user goes to bed at night and wishes to know whether a low glucose level alarm may sound during the night.

This embodiment of the invention includes a predictive alarm avoidance feature that is described hereafter. When the user foresees that he will be unavailable to act on an alarm in the near future, such as, for example, in the case where the user knows he will enter a meeting within the next 30 minutes, the user initiates the process of analyzing his current CGM glucose level and pump calculated IOB information to determine if the user's glucose level is likely be at in a range that the cause the device to produce an alarm during the meeting.

Using a controller that is programmed with appropriate software and hardware commands to carry out the functions required to perform the predictive alarm avoidance embodiment, the user enters the time horizon moving forward that he will be unavailable to take corrective actions if an alarm is presented. This entry is similar to the entry for the number of hours to mute an alarm in the current Freestyle Navigator® Continuous Glucose Monitoring System.

Based on the time horizon entered by the user, and other information found in the memory associated with the CGM and pump device, for example, but not limited to, the current CGM glucose level reading, the current IOB reading, the current bolus calculator parameters, and the current low and high reading settings, the processor calculates whether the user will be in one of three states in the future: a) a state where his glucose profile is adequate; b) in a carbohydrate deficient state, that is, a low glucose level state; and c) an insulin deficient state, that is, the user is in a hyperglycemic state during the time that he will not be able to make an adjustment to his pump. The following example illustrates this process.

Example 1

Assuming a user wishes to avoid an alarm where, and at the time he is commanding the controller to perform this calculation, the following values are pertinent to the calculation:

target threshold: 110 mg/dL,
high alarm threshold: 240 mg/dL,
lower alarm threshold: 70 mg/dL;
carbohydrate ratio: 1 unit of insulin for 15 grams of carb;
insulin sensitivity factor (ISF): 1 unit of insulin for 50 mg/dL; and
insulin action time: 5 hours.

In the case where the user will be unavailable or unwilling to take corrective action if he is presented with an alarm for the next three hours, the processor calculates a glucose level profile of the user utilizing the above factors to determine whether the user's glucose profile will stay in an acceptable range, or if the profile will result in either a hypo- or hyper-glycemic state. In this case, with the above factors, the calculation reveals that the user would have an adequate glucose profile where the current CGM glucose value is 150 mg/dL and the current IOB is 1.1 units. Using methods well known by those in the art, the calculations carried out by the processor show that in five hours, the user's glucose level will decrease by 55 mg/dL (IOB*ISF), which is a glucose decline rate of 11 mg/dL per hour. Thus, during the three hours that the user will be unavailable or unwilling to take action to correct an alarm, the user's glucose level is estimated to be approximately 117 mg/dL (or, a 33 mg/dL decrease in glucose level from the user's current glucose level), which, for this user, is an acceptable glucose level.

Now considering the case where the user's current CGM glucose value is 150 mg/dL and the pump history (stored in the memory associated with the pump or controller) indicates a current IOB of 3.1 units. Using these starting values, the processor calculates that in five hours the user's glucose level will decrease by 155 mg/dL, which is a glucose decline rate of 31 mg/dL per hour. Thus, if the user is unavailable or unwilling to take corrective action in the next three hours, his glucose level will fall to around 57 mg/dL (a 93 mg/dL decrease in glucose level from the user's current glucose level), which is a carbohydrate deficient state.

Once the processor and controller knows that the user will be in a carbohydrate deficient state, the processor can recommend, for example, one or more of the following actions to the user using the display of the controller:

a) instruct the user to eat X grams of carbohydrates now or later to avoid the low glucose level, the value of X being calculated as X=(target minus future low)/ISF*carb ratio which is equal to (110 minus 57)/50*1.5=15.9 grams of carbohydrates; or b) instruct the user to reduce the basal rate of his insulin pump by using a temporary basal rate on the pump. The rate and duration of the temporary basal race is determined by the user using an interface on the device that can be interacted with by the user to cause the processor of the device to compute the temporary basal rate. For example, the controller may provide the user with the information he needs to program the processor of the device to reduce insulin delivery by X units per hour in the next three hours to i) stay within the target glucose level range, where X can be calculated as X=(target minus future low)/ISF/time horizon which is equal to (110 minus 57)/50/3 equals 0.354 units per hour (high reduction) or ii) maintain the user's glucose level above the low alarm threshold X=(low threshold minus future low)/ISF/time horizon equal (70 minus 57)/50/3 equals 0.087 units per hour (lower reduction);

c) the user may also be given the option of increasing the time horizon of the calculations, especially if the recommended reduced insulin amount is greater than the current basal rate, in order to bring about a more conservative reduction in the basal rate. For example, instead of reducing the amount of insulin delivered within the next three hours, the user may extend the time of insulin delivery to five hours.

If the user is watching a movie in a theatre, for example, the user may choose scenario a). If the user performs the calculation right before going to bed, or before taking a short nap, then he may choose scenario b) (assuming that the user's basal rate is greater than 0.087 units per hour or 0.35 per hour).

In a further example, a user's initial CGM glucose level is 280 mg/dL and the pump history indicates that the user's current IOB is 3.1 units. In this case, the processor calculates that in five hours, the user's glucose level will decrease by 155 mg/dL, which is a glucose level decline rate of 31 mg/dL per hour. With this glucose level decline rate, during the next three hours when the user is unavailable or unwilling to take corrective action, the user's glucose level is estimated by the processor to be around 187 mg/dL (a decrease of 93 mg/dL in glucose level from the user's current level), which could mean that the user will be in an insulin deficient state.

Given this calculation, the controller may also determine whether or not more insulin should be recommended to be taken by the user to avoid this possibly insulin deficient state this case, in five hours, based on the JOB, the user's glucose level can be estimated at 125 mg/dL, which a slightly above the user's target glucose level, so the controller and processor of the device may recommend slightly more insulin.

Alternatively, the device may recommend that the user does not need to do anything now or that he could choose to give himself a little more insulin (X units) using an extended bolus feature of the pump where:

$X$=the (predicted glucose level after insulin action time)−(the target glucose level)/ISF which is equal to 0.3 units, and Time duration=the user entered time horizon which is equal to three hours.

An embodiment of the controller of the present invention includes an appropriate User Interface (UI). This user interface is presented by the processor to the user and is formed by processor in accordance with appropriate software commands that have programmed the processor to operate accordingly. The user interface is user friendly to facilitate the user in making the appropriate pump changes. For example, the device should automatically initiate the UI process for temporary basal reduction in case b) and c) described above. Those skilled in the art will understand that the UI may take many different forms without departing from the scope of the present invention.

Because of the acute affect of hypoglycemia, a user is likely to use the above described process to avoid low-alarm occurrence. However, it is conceivable that a similar strategy can be used to avoid exposure to the hazards of hyperglycemia.

Not only can alarms be avoided using the various embodiments of the invention described above, but using a combined CGM and pump device, the actual state of low glucose level, or hypoglycemia, can be avoided. This further enhances the safety and usability of such CGM devices and insulin delivery pumps. Such an approach is also advantageous when compared to using a CGM based projected alarm feature alone which can result in annoying false positives and has much more limited future time projection. The described approach is also superior to muting an alarm to avoid the nuisance of repeated alarms and is also less annoying than a persistent projected low alarm. The user initiated, on-demand nature of the design and the pump control modification UI process integration affords better user control and allows more proactive user intervention to reduce glycemic variability. The embodiments of the invention described above are also advantageous because they can be used as a separate bedtime basal analysis to adjust the basal insulin rate slightly before going to bed. Such an adjustment is especially useful if the user if in a carbohydrate deficient state and does not wish to eat any food before going to bed, thus giving the user the option of reducing the basal rate of insulin delivery before going to bed.

Low glucose or hypoglycemia alarms are typically incorporated into continuous glucose monitoring systems to alert the user to potentially dangerous low glucose levels. For example, the low glucose alarm in the Freestyle Navigator® Continuous Glucose Monitoring System, distributed by Abbott Diabetes Care, is sounded when a user's glucose level falls below a user-defined low glucose threshold. This type of alarm may be subject to false triggering due to sensor signal anomalies such as sensor drop-outs, which are temporary and fully-recoverable signal attenuations believed to be associated with the application of pressure on the percutaneous sensor and/or transmitter as may occur during sleep.

The frequency of these false low-glucose alarms may be increased during closed-loop insulin delivery as the control algorithm will attempt to normalize glucose levels, increasing the percentage of time spent in or near the euglycemic range. Sensor drop outs that occur during hyperglycemia are less likely to trigger low glucose alarms because of these elevated glucose levels. In such a case, sensor drop outs may not sufficiently attenuate the sensor signal to elicit this response. However, if a user's glucose level is maintained closer to the euglycemic (acceptable, that is, neither hypo- nor hyperglycemic) range, as is expected during close-loop control, there is an increased likelihood that sensor drop-out will result in signal attenuation sufficient to cross the low glucose alarm threshold, which results in the presentation of an alarm condition to the user.

Under closed-loop conditions, where the presence of a closed-loop insulin delivery algorithm offers the additional hazard mitigation of the automatic reduction or suspension of insulin delivery based upon real-time glucose level measurements (or based upon the recent history of glucose readings), an alternative low glucose alarm approach may be preferred. In this embodiment, the low glucose level alarm is triggered when a low glucose threshold is exceeded for a clinically significant duration.

Various embodiments of such a delayed low glucose alarm are possible. For example, the alarm may be programmed to sound (1) after X minutes of continuous glucose measurements had been detected below some critical glucose value Y, where Xi=O; Yi=40 mg/dl; where X2=30; Y2=45 mg/dl; and where X3=120; Y3=60 mg/dl; or (2) After a continuous glucose measurement had been detected below some critical threshold A and had not recovered to either that critical threshold A or some intermediary threshold B within some specified duration (A' and B'); or (3) After some cumulative measure of time and duration below a low-glucose threshold, such as when the integral of some low glucose threshold minus the glucose profile exceeds a specified value before the continuous glucose level measurements have recovered to some specified value; or (4) After X minutes of closed loop insulin delivery rate (or total volume administered) below some specified threshold. In this case, insulin delivered is treated as a surrogate for measured glucose level due to the anticipated function of the control algorithm programmed into the software that is operating in the controller and/or pump.

Such an alarm approach is likely to reduce the frequency of false low glucose alarms by allowing for the possibility of the complete or partial recovery from the sensor-drop out to occur prior to the alarm presentation to the user. This loosening of alarm conditions is enabled by the increased safety to the user associated with the reduced or discontinued insulin infusion upon low continuous glucose values that is offered by a close-loop insulin level algorithm.

In another one embodiment of the invention, critical glucose level values are used to define the time allowed before the alarm sounds, resulting in a delayed alarm. For example, the time allowed value could be any appropriate function of glucose level, such as, for example only, and not limited to, a linear relationship.

For example, in one embodiment, the processor re-evaluates the time allowed before the alarm is sounded at every newly received glucose level measurement which is below some predefined or user set value. Using such an approach, if the glucose level is at 60 mg/dL (and previously above 60 mg/dL), then the time until the alarm sounded would be determined to be 60 minutes. One minute later, when the next glucose level value is calculated, the "time until alarm sound" may be calculated to be the lesser of 59 minutes, that is, 60 minutes decremented by one, and the time associated with a linear function; which may be, for example, 3 minutes for every 1 mg/dL that the glucose value is below 60 mg/dL. Thus, if the second glucose value is 55 mg/dL, a decrease in glucose of 15 mg/dL, then the new "time until alarm sound" will be 45 minutes (60 minutes-(3 minutes per mg/dL-.times.15 mg/dL). This determination is repeated for every glucose value received until the alarm sounds or the user's glucose level is greater than 60 mg/dL. Various approaches to this problem may be used individually or in combination in order to minimize false hypoglycemic alarms due to drop outs.

Yet another embodiment of the present invention utilizes model based variable risk determinations to calculate an alarm delay to prevent the annunciation of false alarms, while still providing acceptable protection against a user entering an unacceptable glucose level condition. When CGM systems are used by persons with good glucose control, either by fully manual means, fully automated closed loop operation, or any hybrid means in between, the users glucose will typically be controlled much closer to the euglycemia range than would otherwise occur. This close control, coupled with the expected error distribution of CGM measurements, means that there will be an increased likelihood of CGM values close to or below the hypoglycemia limit. In addition to CGM calibration error, certain CGM signal distortion phenomena such as night time drop-outs also increase the likelihood of an underreported glucose value by the CGM system.

The combination of the three aforementioned factors interacts with standard hypoglycemia detectors to produce a higher incidence of false alarm rates. One embodiment of the invention designed to deal with this problem has been described above. Other approaches are also possible, and intended to be within the scope of the present invention, such as raising the importance and persistency of alarms depending on the length of time the alarm condition has existed without action by the user. Such approaches allow for false hypoglycemic alarms due to a combination of the three aforementioned factors to be minimized.

There will, however, be instances where the patient's physiology and activity temporally pushes their glucose profile out of euglycemia and into either a higher likelihood of hypoglycemia or hyperglycemia. Examples of events where hyperglycemia is more likely would be after exercise, of after a meal where the user failed to receive an insufficient prandial bolus of insulin.

If the user has a system including a CGM and an insulin delivery pump, information from the devices can be pooled or shared, and a model-based monitoring system can be used to modify the alarm mechanism to more efficiently minimize false alarms without imposing unnecessary risk to the patient. Using the information available from the CGM glucose monitor and insulin delivery system, as well as other information entered by the user whenever available (for example, the amount of exercise, state of health, and the like), a model-based system defined by appropriate software commands running on a processor of a controller can perform a prediction of glucose in terms of best estimate and upper/lower bounds for the present time up to a finite horizon in the future. Such a system can be achieved, for example, by implementing the user's model in the form of a Kalman Filter framework, where both the best estimate and variance of each model state is estimated, predicted, and modeled.

Using the present-to-near-future best estimate and bounds, the user's most likely temporal range can be inferred. For example, assume the hypoglycemic detection mechanism of the programming of the controller or pump has 3 levels: 1) wait 30 minutes when the CGM determined glucose level crosses a 60 mg/dL threshold; 2) wait 15 minutes when the CGM determined glucose level crosses a 50 mg/dL threshold, and 3) alarm immediately when the CGM glucose level crosses a 45 mg/dL threshold. A Kalman framework may be used to determine the likelihood for a predicted future glucose level, given the user's current CGM glucose level and other insulin delivery history. This mechanism is implemented "as is" when the model's temporal glucose range suggests the lowest hypoglycemic likelihood. As the likelihood reaches the middle-range risk, then the mechanism is implemented with a 50% shortening of the pre-set delay for sounding the hypoglycemic alarm. For example, the detection levels set forth above may be modified as follows: 1') wait 15 minutes when the CGM glucose level crosses the 60 mg/dL threshold; 2') wait 7.5 minutes when the CGM glucose level crosses the 50 mg/dL threshold, and 3') alarm immediately when the CGM glucose level crosses the 45 mg/dL threshold. When the highest risk of hypoglycemic likelihood is determined, the alarm threshold has 0 delay.

In another embodiment, the same mechanism is implemented, that is: a) wait 30 minutes when the CGM glucose level crosses the 60 mg/dL threshold; b) wait 15 minutes when the CGM glucose level crosses the 50 gm/dL threshold; and 3) alarm immediately when the CGM glucose level crosses the 45 mg/dL threshold) when the model' temporal glucose range suggests the lowest hypoglycemic likelihood. In the middle-range risk, the same delays are retained, but the threshold values are increased, such as, for example: a') wait 30 minutes when the CGM glucose level crosses the 60+5 mg/dL threshold; b') wait 15 minutes when the CGM glucose level crosses the 50+5 mg/dL threshold; and c') alarm immediately when the CGM glucose level crosses the crosses 45+5 mg/dL threshold.

In yet another embodiment, a hybrid of the two previous embodiments may be used. In such an embodiment, both the threshold values and the delay time may be adjusted based on the temporal glucose range determined by the model.

The same types of mechanisms may be applied to hyperglycemia detection, with the tiered thresholds increasing in the order of threshold values. For example, where the CGM glucose level crosses a 180 mg/dL threshold the longest delay time is implemented; where the CGM glucose level crosses a 200 mg/dL threshold, a shorter delay time is implemented before sounding an alarm; and where the CGM glucose level crosses a 220 gm/dL threshold, an even shorter delay time is implemented, up to a maximum threshold with a zero delay time.

While several specific embodiments of the invention have been illustrated and described, it will be apparent that various modifications can be made without departing from the spirit and scope of the invention. Accordingly, it is not intended that the invention be limited, except as by the appended claims.

What is claimed is:

1. A continuous glucose monitoring system comprising:
   a glucose monitoring medical device configured to be coupled externally to a body of a user, the glucose monitoring medical device comprising:
      a glucose sensor configured for implantation into the body of the user and for detecting a glucose level of the user,
      a processor, and
      a wireless communication unit communicatively coupled with and configured to wirelessly communicate with an electronic device of the system; and
   an electronic device comprising:
      a processor,
      a wireless communication unit communicatively coupled with and configured to wirelessly communicate with the wireless communication unit of the glucose monitoring medical device, and
      a memory operably coupled to the processor, wherein the memory includes instructions stored therein that, when executed by the processor, cause the processor to:
         receive a measurement of the glucose level of the user from the glucose monitoring medical device;
         determine that the glucose level of the user has crossed a glucose threshold associated with a glucose alarm;
         delay an initial output of the glucose alarm by the electronic device for a delay time, wherein the delay time comprises a duration of time after the determination that the glucose level has crossed the glucose threshold; and
         cause the initial output of the glucose alarm after the delay time if the glucose level exceeds the glucose threshold throughout the delay time.

2. The system of claim 1, wherein the glucose threshold is settable by the user.

3. The system of claim 1, wherein the system is configured such that the glucose threshold is preprogrammed to the memory of the electronic device.

4. The system of claim 1, wherein the system is configured such that the glucose threshold is associated with hyperglycemia.

5. The system of claim 1, wherein the electronic device further comprises a display incorporating a graphical user interface, wherein the memory comprises instructions that, when executed by the processor of the electronic device, cause the processor to display the glucose alarm in the graphical user interface after the delay time.

6. The system of claim 5, wherein the display is a touch screen capable of responding to user activation.

7. The system of claim 1, wherein the continuous glucose monitoring system further comprises a remote device in wireless communication with the electronic device.

8. The system of claim 7, wherein the remote device is in further wireless communication with the glucose monitoring medical device through the electronic device.

9. The system of claim 1, wherein the duration of time is an annunciation delay time and the initial output of the of the glucose alarm is an annunciation of the glucose alarm.

10. The system of claim 1, wherein the duration of time of the delay time is a first duration of time, the glucose threshold is a first glucose threshold, and the memory includes instructions that, when executed by the processor, cause the processor of the electronic device to:
   determine that the glucose level of the user has crossed a second glucose threshold associated with the glucose alarm, wherein the second glucose threshold is greater than the first glucose threshold; and
   delay the output of the glucose alarm for a second delay time, wherein the second delay time comprises a second duration of time, wherein the second duration of time is shorter than the first duration of time.

11. The system of claim 1, wherein the duration of time of the delay time is a first duration of time, the glucose threshold is a first glucose threshold, and the memory includes instructions that, when executed by the processor, cause the processor of the electronic device to:
determine that the glucose level of the user has crossed a second glucose threshold associated with the glucose alarm, wherein the second glucose threshold is greater than the first glucose threshold; and
cause an output of the glucose alarm without delay upon determination that the glucose level has crossed the second glucose threshold.

12. The system of claim 1, wherein the memory includes instructions that, when executed by the processor of the electronic device, cause the processor to:
provide a recommendation to control the glucose level of the user, wherein the recommendation is based on the detected glucose level.

13. The system of claim 12, wherein the recommendation includes the user ingesting an amount of carbohydrates.

14. The system of claim 12, wherein the recommendation includes reducing a basal rate of a medication delivery device.

15. The system of claim 12, wherein the recommendation includes increasing a time horizon of a medication delivery device of the user.

16. A method of delaying output of a glucose alarm in a continuous glucose monitoring system, the method comprising:
detecting, by one or more processors of an electronic device and using a glucose sensor of a glucose monitoring medical device, a glucose level of a user, wherein the electronic device is communicatively coupled with the glucose monitoring medical device, the glucose monitoring medical device is configured to be coupled externally to a body of the user, and the glucose sensor is configured for implantation into the body of the user;
determining, by the one or more processors, that the glucose level of the user has crossed a glucose threshold associated with the glucose alarm;
delaying, by the one or more processors, an initial output of the glucose alarm for a delay time, wherein the delay time comprises a duration of time after the determination that the glucose level has crossed the glucose threshold; and
causing, by the one or more processors, the initial output of the glucose alarm after the delay time if the glucose level exceeds the glucose threshold throughout the delay time.

17. The method of claim 16, further comprising receiving, by the one or more processors, a value of the glucose threshold from the user.

18. The method of claim 16, wherein the electronic device is configured such that the glucose threshold is preprogrammed to the memory of the electronic device.

19. The method of claim 16, wherein the electronic device is configured such that the glucose threshold is associated with hyperglycemia.

20. The method of claim 16, wherein the electronic device further comprises a display incorporating a graphical user interface, and the method further comprises displaying the glucose alarm in the graphical user interface after the delay time.

21. The method of claim 16, wherein the duration of time is an annunciation delay time and the initial output of the of the glucose alarm is an annunciation of the glucose alarm.

22. The method of claim 16, wherein the duration of time of the delay time is a first duration of time, the glucose threshold is a first glucose threshold, and the method further comprises:
determining, by the one or more processors, that the glucose level of the user has crossed a second glucose threshold associated with the glucose alarm, wherein the second glucose threshold is greater than the first glucose threshold; and
delaying, by the one or more processors, the output of the glucose alarm for a second delay time, wherein the second delay time comprises a second duration of time, wherein the second duration of time is shorter than the first duration of time.

23. The method of claim 16, wherein the duration of time of the delay time is a first duration of time, the glucose threshold is a first glucose threshold, and the method further comprises:
determining, by the one or more processors, that the glucose level of the user has crossed a second glucose threshold associated with the glucose alarm, wherein the second glucose threshold is greater than the first glucose threshold; and
causing, by the one or more processors, an output of the glucose alarm without delay upon determination that the glucose level has crossed the second glucose threshold.

24. The method of claim 16, further comprising:
providing, by the one or more processors, a recommendation to control the glucose level of the user, wherein the recommendation is based on the detected glucose level.

25. The method of claim 24, wherein the recommendation includes the user ingesting an amount of carbohydrates.

26. A non-transitory computer-readable medium comprising instructions which, when executed by one or more processors of an electronic device, are configured to cause the one or more processors to:
detect, using a glucose sensor of a glucose monitoring medical device, a glucose level of a user, wherein the electronic device is communicatively coupled with the glucose monitoring medical device, the glucose monitoring medical device is configured to be coupled externally to a body of the user, and the glucose sensor is configured for implantation into the body of the user;
determine that the glucose level of the user has crossed a glucose threshold associated with the glucose alarm;
delay an initial output of the glucose alarm for a delay time, wherein the delay time comprises a duration of time after the determination that the glucose level has crossed the glucose threshold; and
cause the initial output of the glucose alarm after the delay time if the glucose level exceeds the glucose threshold throughout the delay time.

27. The non-transitory computer-readable medium of claim 26, wherein the instructions are further configured to cause the one or more processors of the electronic device to receive a value of the glucose threshold from the user.

28. The non-transitory computer-readable medium of claim 26, wherein the electronic device is configured such that the glucose threshold is preprogrammed to the memory of the electronic device.

29. The non-transitory computer-readable medium of claim 26, wherein the electronic device is configured such that the glucose threshold is associated with hyperglycemia.

30. The non-transitory computer-readable medium of claim 26, wherein the electronic device further comprises a display incorporating a graphical user interface and wherein the instructions are further configured to cause the one or more processors to display the glucose alarm in the graphical user interface after the delay time.

* * * * *